United States Patent [19]

Miyata et al.

[11] Patent Number: 5,683,347
[45] Date of Patent: Nov. 4, 1997

[54] BALLOON CATHETER

[75] Inventors: Shinichi Miyata, Yokohama; Takashi Kawabata, Hasuda; Tetsuo Toyokawa; Kouichi Sakai, both of Yokohama, all of Japan

[73] Assignee: Nippon Zeon Co., Ltd., Tokyo, Japan

[21] Appl. No.: 508,885

[22] Filed: Jul. 28, 1995

Related U.S. Application Data

[62] Division of Ser. No. 125,843, Sep. 24, 1993, Pat. No. 5,460,607.

[30] Foreign Application Priority Data

| Sep. 30, 1992 | [JP] | Japan | 4-285093 |
| Sep. 30, 1992 | [JP] | Japan | 4-285094 |
| Nov. 30, 1992 | [JP] | Japan | 4-343355 |
| Nov. 30, 1992 | [JP] | Japan | 4-343356 |

[51] Int. Cl.⁶ ............................................. A61N 1/362
[52] U.S. Cl. ............................ 600/18; 604/256; 604/103
[58] Field of Search ........................... 604/96, 256, 164, 604/167, 9, 264, 103; 606/159; 600/16, 17, 18

[56] References Cited

U.S. PATENT DOCUMENTS

| 4,261,339 | 4/1981 | Hanson et al. |
| 4,324,262 | 4/1982 | Hall ........................... 604/54 X |
| 4,422,447 | 12/1983 | Schiff. |
| 4,444,186 | 4/1984 | Wolvek et al. |

(List continued on next page.)

FOREIGN PATENT DOCUMENTS

| 0279959 | 8/1988 | European Pat. Off. |
| 0340304 | 11/1989 | European Pat. Off. |
| 2350110 | 5/1977 | France. |
| 62-114565 | 5/1987 | Japan. |
| 63-206255 | 8/1988 | Japan. |
| WO 80/02366 | 11/1980 | WIPO. |
| WO 86/00010 | 1/1986 | WIPO. |

OTHER PUBLICATIONS

European Search Report, Dec. 15, 1995.

*Primary Examiner*—Mark Bockelman
*Attorney, Agent, or Firm*—Nikaido Marmelstein Murray & Oram LLP

[57] ABSTRACT

A balloon catheter used for intra-aortic balloon pumping (IABP). In the balloon catheter, an outer diameter of a catheter tube is not made constant in the axial direction. Rather, the outer diameter of the catheter tube from a hemostatic valve to a bifurcation, the portion which is positioned outside the patient's blood vessel, is made 3 to 30 percent larger than the outer diameter of the catheter tube from the balloon portion to the hemostatic valve, which is positioned inside the patient's blood vessel. The bifurcation has a first passage and a second passage. The first passage is communicating with a shuttle gas port and is disposed straight along the direction of the axial center of the catheter tube. In the balloon catheter, improvements in a channel resistance of a shuttle gas and in the response can be expected compared with the conventional balloon catheter, where the blood pressure measurement port (the second passage) was disposed straight along the direction of the axial center of the catheter tube and the outer diameter of the catheter tube was made constant in the axial direction.

9 Claims, 18 Drawing Sheets

U.S. PATENT DOCUMENTS

| | | | |
|---|---|---|---|
| 4,467,790 | 8/1984 | Schiff. | |
| 4,473,067 | 9/1984 | Schiff. | |
| 4,569,332 | 2/1986 | Schiff et al.. | |
| 4,692,148 | 9/1987 | Kantrowitz et al.. | |
| 4,857,062 | 8/1989 | Russell | 604/256 |
| 4,865,593 | 9/1989 | Ogawa et al.. | |
| 4,921,483 | 5/1990 | Wijay et al. | 604/96 |
| 4,931,036 | 6/1990 | Kanai et al. | 600/18 |
| 4,943,275 | 7/1990 | Stricker | 600/18 |
| 4,994,018 | 2/1991 | Saper | 600/18 |
| 5,100,386 | 3/1992 | Inoue | 604/103 |
| 5,125,904 | 6/1992 | Lee. | |
| 5,137,513 | 8/1992 | McInnes et al. | 604/96 |
| 5,147,336 | 9/1992 | Wendell et al. | 604/283 |
| 5,195,972 | 3/1993 | Inoue | 604/103 |
| 5,195,980 | 3/1993 | Catlin. | |
| 5,213,577 | 5/1993 | Kratzer | 604/96 X |
| 5,254,097 | 10/1993 | Schock et al.. | |
| 5,269,771 | 12/1993 | Thomas et al.. | |
| 5,308,319 | 5/1994 | Ide et al. | 600/18 |
| 5,308,354 | 5/1994 | Zacca et al. | 606/159 |
| 5,334,160 | 8/1994 | Ellis | 604/167 |
| 5,460,607 | 10/1995 | Miyata et al. | 604/96 |

(JIS 43)

(JIS 50)

BALLOON CATHETER

This is a divisional, of application Ser. No. 08/125,843 filed Sep. 24, 1993 now U.S. Pat. No. 5,460,607.

BACKGROUND OF THE INVENTION

1. Field of the Invention

The present invention relates to a balloon catheter used for intra-aortic balloon pumping (IABP technique) for treatment of acute cardiac insufficiency etc.

2. Description of the Related Art

In the IABP technique, cardiac insufficiency and other deterioration of cardiac functions are treated by inserting into the aorta a balloon catheter comprised of a balloon portion and catheter tube made of a synthetic polymer material and introducing or releasing a shuttle gas into or from the balloon portion through the catheter tube by a driving console so as to make the balloon portion expand and contract in timing with the heart beating and thereby assist the heart beatings.

As the balloon catheter used for the IABP technique, there are known the balloon catheters disclosed in Japanese Unexamined Patent Publication (Kokai) No. 63-206255 and Japanese Unexamined Patent Publication (Kokai) No. 62-114565. In these balloon catheters, it is necessary to detect the heart beating of the patient in order to make the balloon portion expand and contract in timing with the heart beating. As a means for detecting the heart beating of a patient, there is the means of attaching electrodes to the surface of the patient's body or in his or her body and detecting the heart beating as an electrical signal.

Further, as a means for detecting the heart beating from the blood pressure of the patient using the balloon catheter, there is the method of detecting the heart beating by providing the front tip portion of the balloon portion with a blood port, inserting an inner tube communicated with the blood port inside the balloon portion and the catheter tube in the axial direction of the same, and measuring the fluctuation in the blood pressure from a blood pressure outlet.

In such a type of balloon catheter, a bifurcation is connected to the proximal end of the catheter tube outside the body. At this bifurcation there are formed a shuttle gas port for introducing or releasing the shuttle gas into or from the catheter tube and the balloon portion and a blood pressure measurement port communicated to the inside of the inner tube. The shuttle gas port is connected to a driving console. This driving console is used to introduce or release the fluid pressure into or from the balloon portion.

In a balloon catheter of such a construction, there were the following problems. That is, since the catheter tube 24 is inserted into the arterial blood vessel of the patient, considering the discomfort of the patient, the catheter tube is preferably made as small as possible in outer diameter. If the outer diameter of the catheter tube is made small, however, the fluid pressure passage formed inside it becomes smaller, the channel resistance rises, and the timing response of the expansion and contraction of the balloon portion driven by the shuttle gas becomes poorer, making it impossible in some cases to effectively achieve a heart assisting action. The period of the expansion and contraction of the balloon portion is 0.6 second assuming a heart beating of 100 beats/minute. The shuttle gas reciprocates in the catheter tube in a time shorter than this period, so the smaller the channel resistance the better.

Therefore, in the past, the outer diameter of the catheter tube was set as large as possible within the range not significantly increasing the discomfort of the patient, and the timing response of the expansion and contraction of the balloon portion was sacrificed to a certain extent. In the conventional balloon catheter, further, since the inner tube could freely move in the radial direction in the catheter tube, when inserting the catheter tube into the arterial blood vessel of the patient by snaking it along the blood vessel, the inner tube would lay irregularly snaked inside the catheter tube. As a result, when the shuttle gas for making the balloon portion expand or contract passed through the clearance between the outer wall of the inner tube and the inner wall of the catheter tube, an eddy flow was produced, the energy loss of the fluid was increased, the efficiency of the driving console was reduced, and the timing response of expansion and contraction could be worse.

Further, the inner tube would flex due to the catheter tube having to be snaked through the twisted portions of the blood vessel in the body and thereby would block the area around where the shuttle gas port intersects with the extension of the catheter tube, thereby possibly causing a large fluid resistance.

SUMMARY OF THE INVENTION

The present invention was made in consideration of these actual circumstances and has as its first object the provision of a balloon catheter which can reduce the channel resistance in the catheter tube through which the shuttle gas passes without increasing the discomfort of the patient and which enables expansion and contraction of the balloon portion with a good response.

The present invention has as its second object the provision of a hemostatic valve which can be used for a balloon catheter, can move in the axial direction on the outer circumference of the catheter tube, can be affixed at any position in the axial direction without crushing the catheter tube, and is excellent in hemostatic action.

The present invention has as its third object the provision of a balloon catheter which can be easily inserted into the blood vessel of the patient, enables the balloon portion to be inserted to the proper position in the blood vessel, and will not be pushed back by the flow of blood.

The present invention has as its fourth object the provision of a balloon catheter which is not reduced in the outer diameter of the catheter tube, is superior in response in expansion and contraction of the balloon portion, can be smoothly inserted into the blood vessel of the patient, and causes little discomfort to the patient.

To achieve the first object, the first aspect of the invention provides a balloon catheter comprising a balloon portion which is inserted into the aorta and expands and contracts to assist the heart beating, a catheter tube which is connected to the proximal end of the balloon portion and introduces and releases shuttle gas into and from the balloon portion, a hemostatic valve attached on the outer circumference of the proximal end of the catheter tube in a manner movable in the axial direction and having a hemostatic sheath portion which has a distal end pushed into an insertion site formed in the blood vessel of the patient so as to plug the insertion site, and a bifurcation to which the proximal end of the catheter tube is connected and having formed therein a shuttle gas port for introducing and releasing shuttle gas into and from the balloon portion, the outer diameter of the catheter tube from the hemostatic valve to the bifurcation being 3 to 30 percent larger than the outer diameter of the catheter tube from the balloon portion to the hemostatic valve.

The bifurcation has formed in it, separate from the shuttle gas port, a blood pressure measurement port for measuring the pressure of the blood taken in from a blood port formed in the distal end of the balloon portion through an inner tube disposed in the balloon portion and the catheter tube. The shuttle gas port is preferably disposed straight along the direction of the axial center of the catheter tube, while the blood pressure measurement port is preferably disposed at a predetermined angle with respect to the axial center of the shuttle gas port.

In the balloon catheter of the first aspect of the present invention, the outer diameter of the catheter tube is not made constant in the axial direction. Rather, the outer diameter of the catheter tube from the hemostatic valve to the bifurcation, the portion which is positioned outside the patient's blood vessel, is made 3 to 30 percent larger than the outer diameter of the catheter tube from the balloon portion to the hemostatic valve, which is positioned inside the patient's blood vessel. This range of percent is set because when less than 3 percent, the effect of the present invention is slight, while if over 30 percent, the outer diameter of the hemostatic sheath portion becomes too large, it becomes difficult to insert this into the skin and tissue of the patient, and its fabrication becomes difficult.

By making the outer diameter of the catheter tube from the hemostatic valve to the bifurcation larger by this range, assuming the thickness of the catheter tube is the same in the axial direction, the inner diameter of the catheter tube from the hemostatic valve to the bifurcation also becomes larger and the channel cross-section at that portion becomes larger as well. As a result, it becomes possible to reduce the channel resistance inside the catheter tube without increasing the discomfort of the patient. The length of the catheter tube from the hemostatic valve to the bifurcation corresponds to about 20 to 35 percent of the entire length of the catheter tube, so making the outer diameter larger at that portion so as to enlarge the channel cross-section is very effective in terms of reducing the internal channel resistance of the catheter tube as a whole. The channel resistance (pressure loss) is inversely proportional to the inner diameter of the catheter tube to the fourth power. If the inner diameter is made 3 to 30 percent larger, the channel resistance can be reduced by the 3 to 30 percent to the fourth power. Since the region of reduction is 5 to 35 percent of the entire length, a more than 10 percent improvement in the channel resistance of the inside of the catheter tube as a whole can be expected. Further, more than a 20 percent improvement can be expected in the response of expansion and contraction of the balloon portion.

To achieve the first object of the present invention, the second aspect of the present invention provides a balloon catheter which has a balloon portion for insertion in the aorta for expansion and contraction, a catheter tube connected to the proximal end of the balloon portion and formed with a shuttle gas passage for introducing and releasing a shuttle gas into and from the inside of the balloon portion, an inner tube communicated with a blood port formed in the distal end of the balloon portion, extending in the balloon portion and the catheter tube in the axial direction, and having a blood passage formed separate from the shuttle gas passage, and a bifurcation formed with a first passage formed with a shuttle gas port communicating with the inside of the shuttle gas passage of the catheter tube and a second passage formed with a blood pressure measurement port communicating with the inside of the inner tube, in the bifurcation, the first passage being disposed straight along the direction of the axial center of the catheter tube and the second passage being disposed at a predetermined angle with respect to the axial center of the first passage.

In the second passage of the bifurcation formed with the blood pressure measurement port, there is preferably attached an inner tube end holder for making the inner tube be disposed eccentrically in the catheter tube so as to contact the inner wall of the catheter tube.

In the balloon catheter of the second aspect of the present invention, since the first passage formed in the bifurcation and communicating with the shuttle gas port is disposed straight along the direction of the axial center of the catheter tube, a 2 percent improvement in the channel resistance of the shuttle gas and a 4 percent improvement in the response can be expected compared with the conventional balloon catheter, where the blood pressure measurement port was disposed straight along the direction of the axial center of the catheter tube.

In particular, if the second passage of the bifurcation formed with the blood pressure measurement port has attached in it an inner tube end holder for making the inner tube be disposed eccentrically so as to contact the inner wall of the catheter tube, a 4 percent improvement in the channel resistance of the shuttle gas and an 8 percent improvement in the response can be expected compared with the conventional balloon catheter, where the inner tube moved freely in the radial direction in the catheter tube. This is because by making the inner tube be disposed eccentrically so as to contact the inner wall of the catheter tube, the channel resistance of the shuttle gas passage inside the catheter tube can be reduced.

To achieve the second object of the present invention, the hemostatic valve has a hemostatic valve body which is attached to the outer circumference of the catheter tube in a manner freely movable along the axial direction, a cap portion which can be screwed with the hemostatic valve body and is attached to the outer circumference of the catheter tube in a manner freely movable along the axial direction, and a holding ring which is attached to the outer circumference of the catheter tube positioned between the hemostatic valve body and cap portion, has a predetermined clearance with the outer circumference of the catheter tube in a state with the hemostatic valve body and cap portion not screwed together, and elastically deforms to press against the outer circumference of the catheter tube by the hemostatic valve body and the cap portion being screwed together more than a predetermined number of turns, the JIS hardness of the holding ring being at least 52 preferably at least 55.

The holding ring may be any elastically deformable material, but for example may be comprised by a rubber tube.

In the hemostatic valve of the present invention, in the state with the hemostatic valve body and cap portion not screwed together, a clearance is formed between the inner circumference of the holding ring and the outer circumference of the catheter tube. As a result, the hemostatic valve can move freely in the axial direction of the catheter tube. When desiring to affix the hemostatic valve at any position in the axial direction of the catheter tube, the hemostatic valve body and the cap portion are screwed together. At that time, the catheter tube would be crushed if these are screwed together by a predetermined number of turns, but in the present invention, use is made of a holding ring with a JIS hardness of at least 52 so the turning torque increases just before the catheter tube is crushed.

Therefore, by stopping the screwing just before the turning torque increases, the catheter tube will not be crushed. Further, in the present invention, there is a sufficient fixing force (catheter holding force) and hemostatic action (pressure resistance) at the position of the number of screw turns just before the catheter tube is crushed. As a result, it is possible to affix the hemostatic valve at any position in the axial direction by a predetermined fixing force and giving a good hemostatic action without crushing the catheter tube.

To achieve the third object of the present invention, the third aspect of the invention provides a balloon catheter which has a balloon portion to be inserted into the aorta for expansion and contraction to assist the heart beating, a catheter tube connected to the proximal end of the balloon portion for introducing and releasing a shuttle gas into and from the balloon portion, and a metal inner tube which extends in the balloon portion and the catheter tube in the axial direction thereof so as not to communicate with the channel of the shuttle gas, the distal end portion of the metal inner tube at the blood port side being treated to increase its flexibility compared with other portions of the metal inner tube.

As a means for increasing the flexibility of the distal end portion of the metal inner tube, in the present invention, use is made of the means of reducing the hardness by heat treatment, the means of reducing the thickness of the distal end portion, the means of forming the bellows-like irregularity at the distal end portion, and the means of providing slits in the distal end portion. Any one or any combination of these may be used.

To insert the balloon catheter of the third aspect of the present invention into the arterial blood vessel of the patient, the balloon portion is wound around the circumference of the metal inner tube to reduce its outer diameter and is inserted in that state.

In the balloon catheter of the third aspect of the present invention, since use is made of a metal inner tube, it is possible to reduce the outer diameter of the inner tube to obtain the desired rigidity. Therefore, it is possible to increase the channel cross-section of the shuttle gas between the catheter tube and the inner tube and the timing response of expansion and contraction of the balloon portion is improved. Further, since only the distal end is made softer, it is possible to insert the balloon catheter easily along the snaking blood vessel and the balloon portion will not be pushed back by the flow of blood after being positioned at the predetermined position in the arterial blood vessel near the heart.

In the balloon catheter of the third aspect of the present invention, by treating the distal end of the metal inner tube in some fashion, the flexibility is increased. Since another member with flexibility is not connected, the joint portion does not become larger. In this respect as well, the insertion of the balloon catheter is easier.

To achieve the fourth object of the present invention, the fourth aspect of the present invention provides a balloon catheter having a balloon portion which is to be inserted into the aorta and expands and contracts to assist the heart beatings and a catheter tube which introduces and releases a shuttle gas into and from the balloon portion, the proximal end of the balloon portion and the distal end of the catheter tube being joined at the outer circumferences of the two ends of a metal connection tube so as not to be superposed over each other.

This was not conceived of in balloon catheters of the prior art designed for strong joining of the balloon portion and the catheter tube.

As the means of joining these members, use may be made of a means such as adhesion by an adhesive or heat bonding.

In the balloon catheter of the fourth aspect of the present invention, since the proximal end of the balloon portion and the distal end of the catheter tube are joined at the outer circumferences of the two ends of the metal connection tube and are not superposed on each other, the outer diameter of the joint portion can be made smaller by about two times the thickness of the balloon (diameter) compared with the conventional balloon catheter without making the outer diameter of the catheter tube smaller. The thickness of the balloon portion is in general from 100 to 150 μm, so the outer diameter of the joint portion can be reduced by about 200 to 300 μm. Further, the outer diameter of the catheter tube is about 3 mm, so the outer diameter of the joint portion can be reduced about 7 to 10 percent compared with the conventional balloon catheter.

DESCRIPTION OF THE PREFERRED EMBODIMENTS

Figure 1:
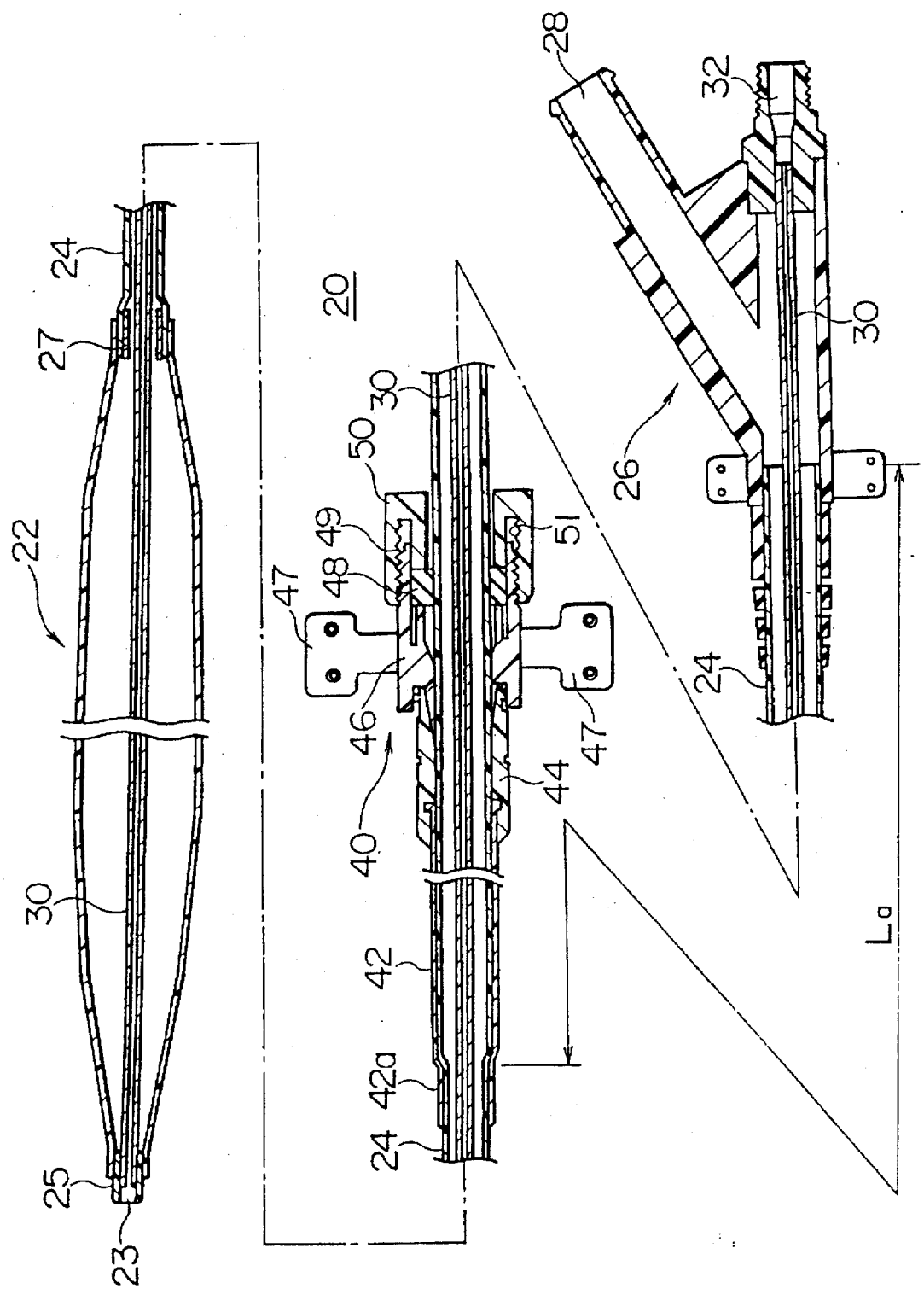
FIG. 1 is a schematic cross-sectional view of a balloon catheter according to a first embodiment of the present invention.

Below, balloon catheters according to preferred embodiments of the present invention will be explained in more detail referring to the drawings.

First Embodiment

As shown in FIG. 1, the balloon catheter 20 according to a first embodiment of the present invention has a balloon portion 22 which expands and contracts in timing with the heart beating. The balloon portion 22 is comprised of a thin film of a thickness of about 100 to 150 µm. The material of the thin film is not particularly limited, but preferably is a material superior in resistance to flexural fatigue, for example, is made of polyurethane. The outer diameter and length of the balloon portion 22 are determined in accordance with the inner volume of the balloon portion 22, which has a great effect on the effect of assisting the heart beatings, the inner diameter of the arterial blood vessel, and the like. The inner volume of the balloon portion 22 is not particularly limited, but may be 30 to 50 cc. The outer diameter of the balloon portion 22 is preferably 14 to 16 mm, and the length is preferably 210 to 270 mm.

At the distal end of the balloon portion 22 there is attached by a means such as heat bonding or adhesion a front tip portion 25 with a blood port 23 formed in it.

At the inner circumference of the front tip portion 25 is attached the distal end of the inner tube 30 by heat bonding or adhesion.

The inner tube 30 extends in the axial direction inside the balloon portion 22 and the catheter tube 24 and is communicated with the later mentioned blood pressure measurement port 32 of the bifurcation 26. The inside of the inner tube 30 is not communicated with the inside of the balloon portion 22. The inner tube 30 positioned in the balloon portion 22 is also used as the guide rod at the time of inserting the balloon catheter 20 in the artery. The contracted balloon portion 22 is wound on it for easy insertion of the balloon portion 22 in the artery.

At the proximal end of the balloon portion 22 at the outer circumference of a metal connecting tube 27 is connected the distal end of the catheter tube 24. The fluid pressure is introduced to or released from the inside of the balloon portion 22 through the catheter tube 24 so as to make the balloon portion 22 expand or contract. The balloon portion 22 and the catheter tube 24 are connected by heat bonding or adhesion by an adhesive such as an ultraviolet ray curable resin.

The material of the catheter tube 24 is not particularly limited, but use may be made of polyurethane, polyvinyl chloride, polyethylene, nylon, etc.

At the proximal end of the catheter tube 24 is connected the bifurcation 26 positioned outside the patient's body. The bifurcation 26 is formed separate from the catheter tube 24 and is affixed by a means such as heat bonding or adhesion, but it may also be formed integrally with the catheter tube 24. At the bifurcation 26 are formed a shuttle gas port 28 for introducing or releasing shuttle gas into or from the inside of the catheter tube 24 and the balloon portion 22 and a blood pressure measurement port 32 communicated with the inside of the inner tube 30.

Figure 5:
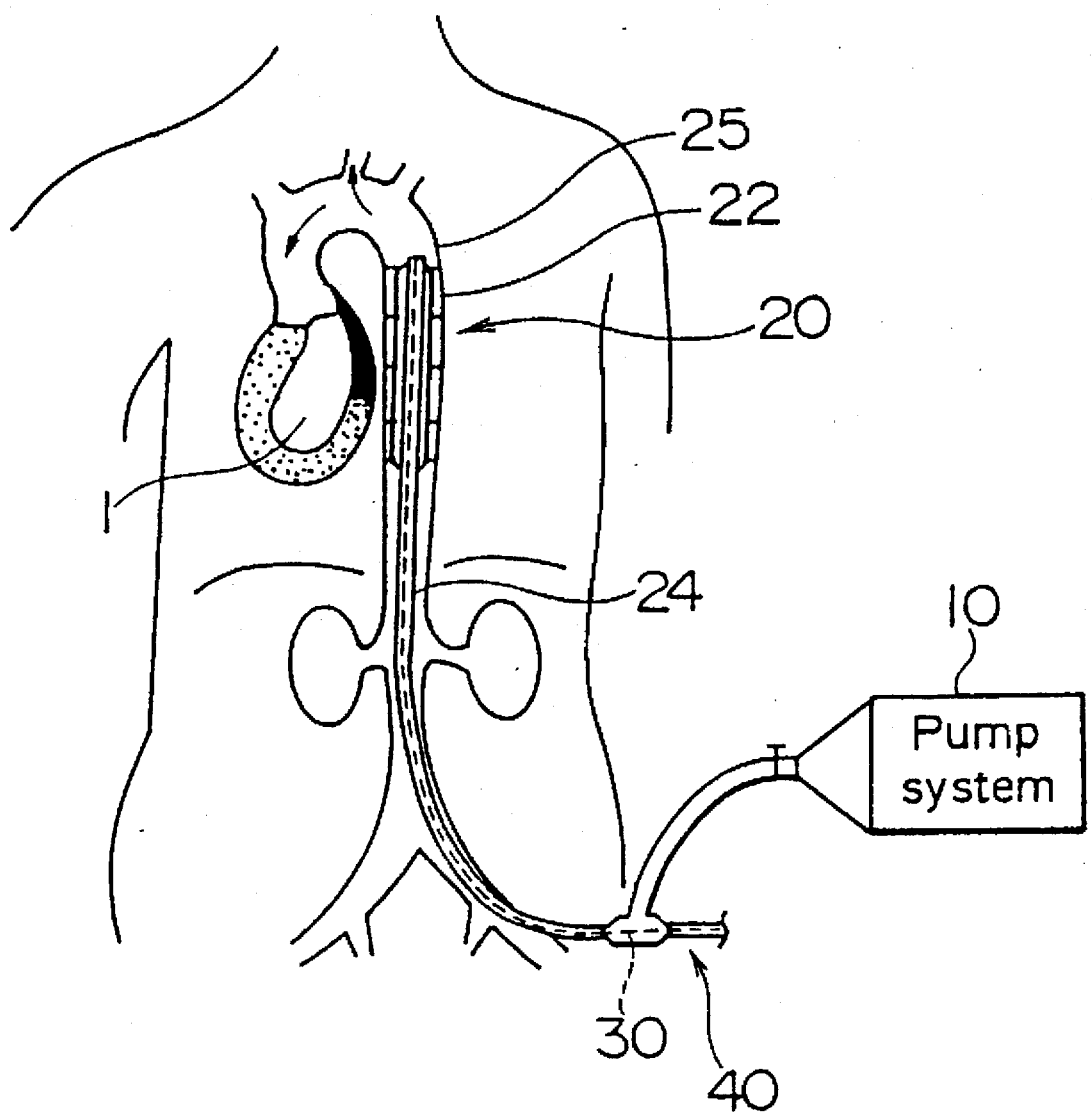
FIG. 5 is a schematic view showing the state of use of the balloon catheter.

The shuttle gas port 28 is connected to a driving console 10, for example, as shown in FIG. 5. This driving console 10 is used to introduce or release the fluid pressure in or from the balloon portion 22. The fluid which is introduced is not particularly limited, but use may be made of helium gas etc., having a small viscosity, so that the balloon portion can expand or contract quickly in accordance with the operation of the driving console 10. The driving console 10 is not particularly limited, but use may be made for example of the one disclosed in Japanese Examined Patent Publication No. 2-39265.

The blood pressure measurement port 32 is connected for example to a blood pressure measurement apparatus, which can measure the fluctuations in the pressure of the arterial blood taken from the blood port 23. The heart beating is detected based on the fluctuations in the blood pressure measured by the blood pressure measurement apparatus, and the driving console 10 shown in FIG. 5 is controlled in accordance with the heart beating to make the balloon portion 22 expand or contract.

In this embodiment, a hemostatic valve 40 is attached at the outer circumference of the catheter tube 24 positioned in front of the bifurcation 26 in a manner to be movable along the axial direction of the catheter tube 24. The hemostatic valve 40 has a hemostatic sheath portion 42 which is pushed at its distal end 42a into the catheter insertion site formed in the patient's blood vessel at the time of insertion of the balloon catheter so as to plug the insertion site in the blood vessel and is positioned outside the patient's blood vessel. The proximal end of the hemostatic sheath portion 42 is connected to a holder base portion 46 through the sheath base end 44. At the outer circumference of the holder base portion 46, the holder 47 is formed projecting outward and a male threaded portion 49 is formed.

Figure 2:
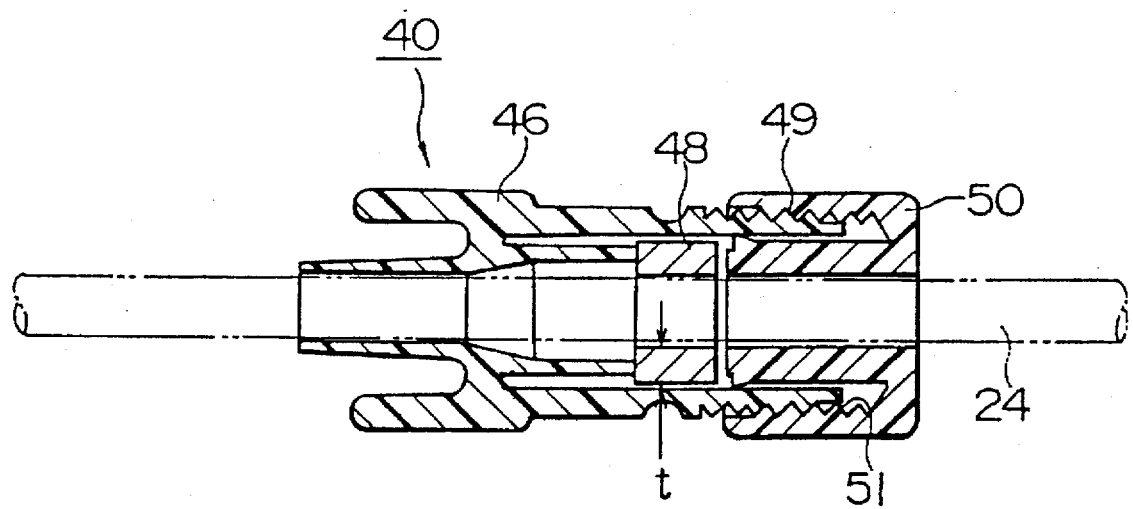
FIG. 2 is a schematic cross-sectional view of a hemostatic valve used in the balloon catheter.

As shown in FIG. 2, a female threaded portion 51 of the cap portion 50 can be screwed on the male threaded portion 49 of the holder base portion 46. A holding ring 48 with elasticity is interposed between the holder base portion 46 and the cap portion 50. By tightening the female threaded portion 51 of the cap portion 50 on the male threaded portion 49 of the holder base portion 46, the holding ring 48 elastically deforms, the inner diameter becomes smaller, the outer circumference of the catheter tube 24 is pressed close against, the hemostatic valve 40 as a whole is affixed to the outer circumference of the catheter tube 24, and the movement in the axial direction is restricted.

In a state where the female threaded portion 51 of the cap portion 50 is not screwed onto the male threaded portion 49 of the holder base portion 46, the inner diameter of the holding ring 48 is larger than the outer diameter of the catheter tube 24 and the hemostatic valve 40 as a whole can be moved freely in the axial direction of the catheter tube 24. The distal end 42a of the hemostatic sheath portion 42 in the hemostatic valve 40, as mentioned earlier, is pushed into the catheter insertion site formed in the patient's blood vessel to plug the insertion site of the blood vessel. The relationship between the catheter insertion site formed in the patient's blood vessel and the position of the catheter tube 24 in the axial direction differs depending on the patient, so the hemostatic sheath portion 42 has to be moved in the axial direction of the catheter tube 24 along with the hemostatic valve 40 and be affixed to the catheter tube 24 at a predetermined position in the axial direction.

In this hemostatic valve 40, the holding ring 48 is made of an elastic material, for example, is made of silicone rubber, fluororubber, natural rubber, polyurethane, etc. In this embodiment, the JIS (Japanese Industrial Standard) hardness of the holding ring 48 is at least 52preferably from 55 to 70. A holding ring 48 having such a hardness can be produced, for example, by casting a rubber material such as silicone rubber.

The inner diameter of the holding ring 48 is preferably 50 to 300 μm larger than the outer diameter of the catheter tube 24. Further, the outer diameter of the holding ring 48 is preferably about 50 to 300 μm smaller than the inner diameter of the hemostatic valve body 46 positioned at the outer circumference of the holding ring 48. Also, the thickness "t" of the holding ring 48 in the radial direction (see FIG. 2) is preferably 0.25 to 1.5 times the outer diameter of the catheter tube 24.

In this embodiment, the outer diameter of the catheter tube 24 is not made constant in the axial direction. Rather, the outer diameter of the catheter tube 24 in the range from the hemostatic valve 40 to the bifurcation 26 is made 3 to 30 percent larger than the outer diameter of the catheter tube 24 from the balloon portion 22 to the hemostatic valve 40. This range of percent is set because when less than 3 percent, the effect of the present invention is slight, while if over 30 percent, the outer diameter of the hemostatic sheath portion 42 becomes too large, it becomes difficult to insert this into the skin and tissue of the patient, and its fabrication becomes difficult.

The outer diameter of the catheter tube 24 from the balloon portion 22 to the hemostatic valve 40 is generally 2.3 to 4.0 mm, so the outer diameter of the catheter tube 24 in the range of the length "La" from the hemostatic valve 40 to the bifurcation 26 is preferably about 2.4 to 5.2 mm. The thickness of the catheter tube 24 is preferably uniform in the axial direction and is preferably 0.05 to 0.4 mm.

The length "La" from the hemostatic valve 40 to the bifurcation 26 is not particularly limited, but about 100 to 200 mm is preferable, or about 5 to 35 percent of the total length of the catheter tube 24.

The catheter tube 24 of which outer diameter is not constant in the axial direction may be produced by following methods.

In a first method, a tube of which outer diameter is 2.4 to 5.2 mm is prepared. The one end of the tube is heated and withdrawn lengthwise in order to make the outer diameter of the one end of the tube reduced to 3 to 30 percent. Accordingly, the catheter tube 24 of which outer diameter is not constant in the axial direction can be produced.

In a second method, a tube of which outer diameter is 2.3 to 4.0 mm is prepared. The one end of the tube is heated and enlarged by a insertion molding rod in order to make the outer diameter of the one end of the tube enlarged to 3 to 30 percent. Accordingly, the catheter tube 24 of which outer diameter is not constant in the axial direction can be produced.

In a third method, two tubes of which outer diameters are 2.3 to 4.0 mm and 2.4 to 5.2 m are prepared. Both ends of the tubes are bonded by an adhesive and the outer bonding portion is formed in taper-shaped. Accordingly, the catheter tube 24 of which outer diameter is not constant in the axial direction can be produced.

By making the outer diameter of the catheter tube from the hemostatic valve 40 to the bifurcation 26 larger by 3 to 30 percent compared with other portions, assuming the thickness of the catheter tube 24 is the same in the axial direction, the inner diameter of the catheter tube 24 from the hemostatic valve 40 to the bifurcation 26 also becomes larger by 3 to 30 percent and the channel cross-section at that portion becomes larger as well. As a result, it becomes possible to reduce the channel resistance inside the catheter tube 24 without increasing the discomfort of the patient.

The length "La" of the catheter tube from the hemostatic valve 40 to the bifurcation 26 corresponds to about 20 to 35 percent of the entire length of the catheter tube 24, so making the outer diameter larger at that portion so as to enlarge the channel cross-section is very effective in terms of reducing the internal channel resistance of the catheter tube 24 as a whole. The channel resistance is inversely proportional to the inner diameter of the catheter tube 24 to the fourth power. If the inner diameter is made 3 to 30 percent larger, the channel resistance can be reduced by the 3 to 30 percent to the fourth power. Since the region of reduction is 5 to 35 percent of the entire length, a more than 10 percent improvement in the channel resistance of the inside of the catheter tube 24 as a whole can be expected. Further, more than a 20 percent improvement can be expected in the response of expansion and contraction of the balloon portion 22.

Note that the outer diameter of the sheath portion 42 positioned at the outer circumference of the catheter tube 24 formed with a large diameter also becomes larger, but the sheath portion 42 is not inserted into the blood vessel of the patient. Just part of its distal end is inserted in the skin and tissue just in front of the patient's blood vessel, so =he discomfort of the patient is not that great.

Next, an explanation will be made of the method of insertion of the balloon catheter 20 using the catheter tube set of this embodiment.

Figure 3A:
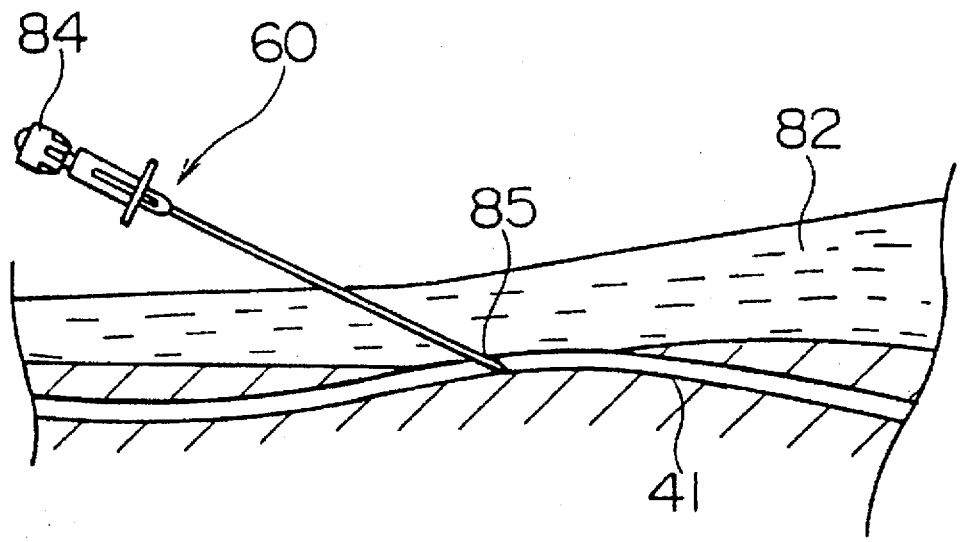
FIGS. 3A to 3D and FIG. 4 are schematic views showing the process of insertion of the balloon catheter.

First, as shown in FIG. 3A, a needle 60 is inserted from the surface of the skin 82 of the patient to position its distal end in the blood vessel 41. Next, a styler 84 inserted through the inside of the needle is pulled out. A guide wire 62 (see FIG. 3B) is inserted into the blood vessel 41 from the hole from which the styler 84 was pulled out.

Figure 3B:
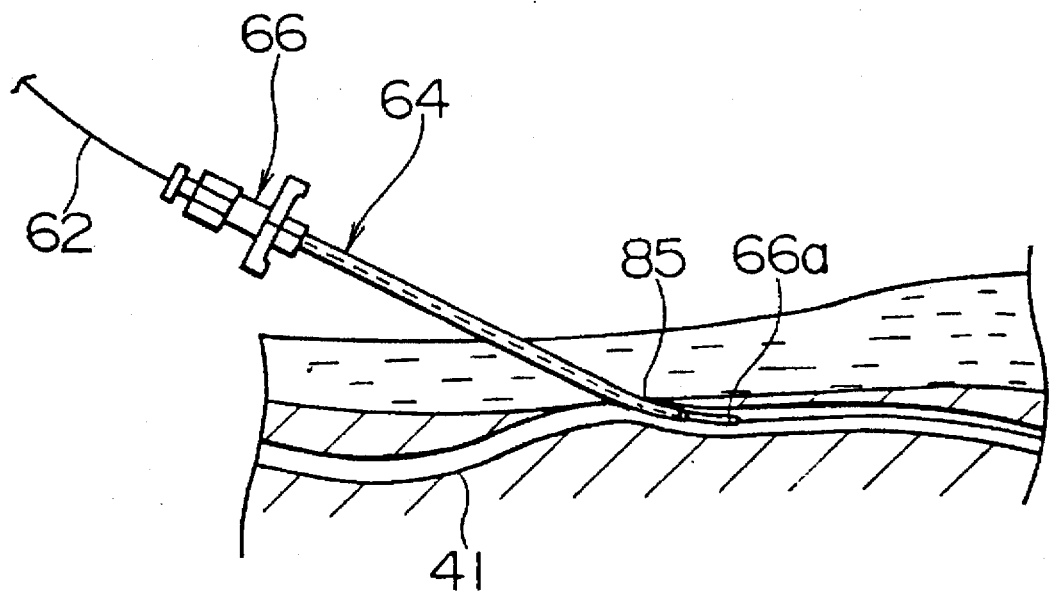

Next, the needle 60 is pulled out along the inserted guide wire 62, then a small diameter dilator (not shown) with a front taper is inserted into the insertion site 85 of the blood vessel along the guide wire 62 to push wider the insertion site 85. Next, the small diameter dilator is pulled out along the guide wire, then, as shown in FIG. 3B, then a tapered cannula dilator 66 is inserted along the guide wire 62 into the blood vessel 41 in the state with the distal end 66a inserted in the cannula 64.

Figure 3C:
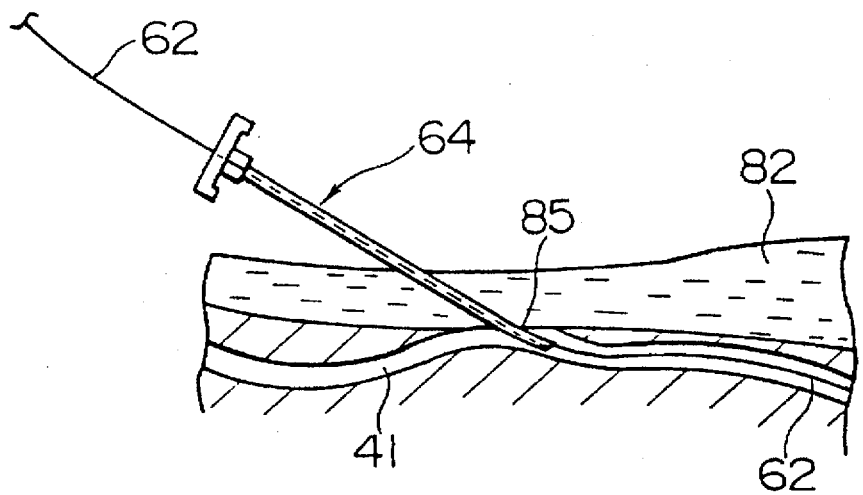

Next, as shown in FIG. 3C, the dilator 66 is pulled out in the state with the distal end of the cannula 64 inserted in the blood vessel 41. Then, the balloon portion 22 and catheter tube 24 of the balloon catheter 20 shown in FIG. 1 are inserted into the blood vessel 41 through the cannula 64. At the time of insertion, the balloon portion 22 is superposed over an outer diameter less than the inner diameter of the cannula 64. Further, at the time of insertion, the guide wire 62 is passed into the inner tube 30 of the balloon catheter 20.

When the balloon portion 22 and catheter tube 24 of the balloon catheter 20 are inserted at the proper positions in the blood vessel 41 through the cannula 64, in the present embodiment, as shown in FIG. 1, a hemostatic valve 40 with a hemostatic sheath portion, attached to the outer circumference of the catheter tube 24 outside the body in a manner freely movable in the axial direction, is inserted along the axial direction of the catheter tube 24 in the direction of the insertion site 85 of the blood vessel 41, that is, the direction of the cannula 64.

Figure 3D:
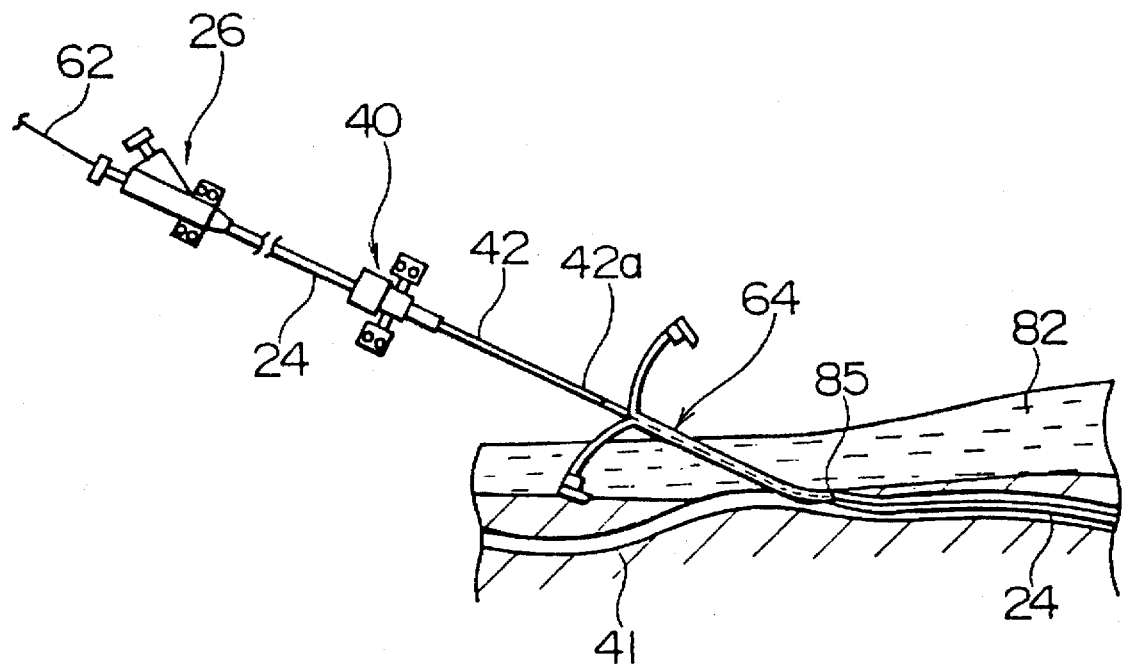

The hemostatic sheath portion 42 is moved along with the hemostatic valve 40 in the direction of the cannula 64 axially along the catheter tube 24, as shown in FIG. 3D, and the cannula 64 is peeled off from the catheter tube 24.

Figure 4:
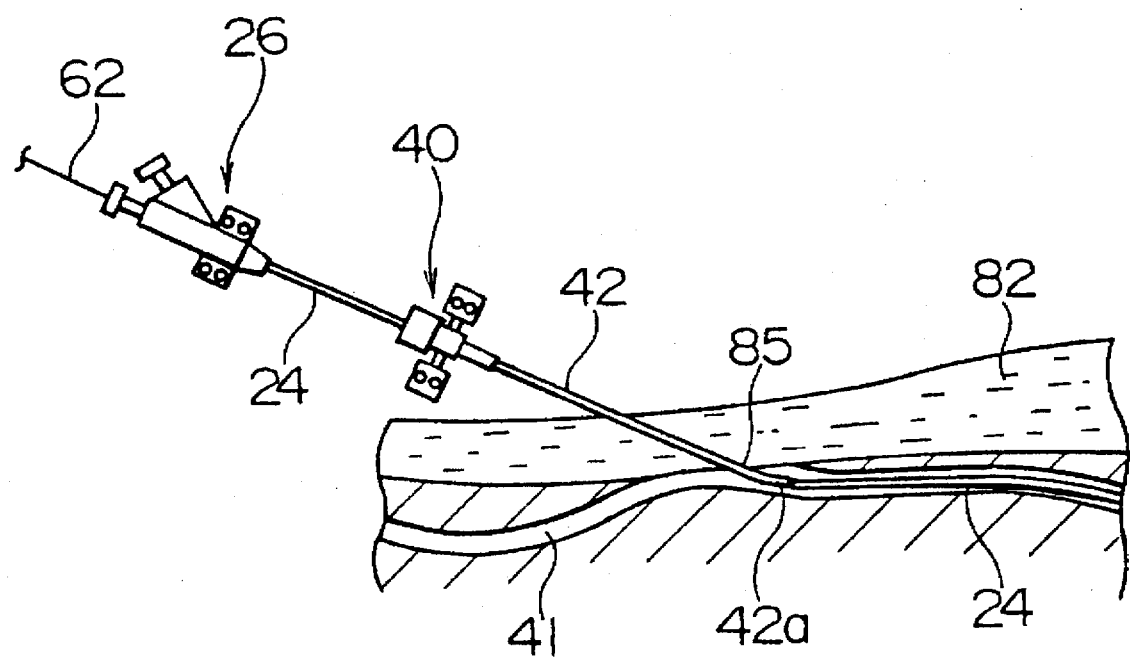

After the cannula 64 is removed, the distal end 42a of the hemostatic sheath portion 42 is inserted in the direction of the blood vessel of the patient, whereby the clearance between the insertion site 85 of the blood vessel and the outer circumference of the catheter tube 24 is plugged and the bleeding is stopped. This state is shown in FIG. 4. Next, the hemostatic valve 40 is used to affix the hemostatic sheath portion 42 to the outer circumference of the catheter tube 24. The hemostatic valve 40 is affixed to the patient's skin. By this, the position of insertion of the catheter tube 24 and the balloon portion 22 is kept from shifting in the longitudinal direction of the blood vessel 41. As shown in FIG. 5, the balloon portion 22 is positioned at a predetermined position inside the arterial blood vessel close to the heart I and made to expand and contract there so as to assist the heart beatings, so it is important that the catheter tube 24 not shift in position in the blood vessel 41.

The bifurcation 26 shown in FIG. 1 is affixed to the skin of the patient and IABP treatment is performed by the balloon catheter 20.

In accordance with the present invention, the hemostatic valve 40 may not necessary be attached to the catheter tube 24. In this embodiment, the potion of the catheter tube in the range of length "La" is directly inserted into the insertion site 85 of the blood vessel so that the opening 85 is plugged on behalf of the hemostatic sheath portion 42. The length "La" from the proximal end of the catheter tube 24 to a changing portion in an outer diameter is not particularly limited, but about 30 to 300 mm is preferable, or about 1.5 to 50 percent of the total length of the catheter tube 24.

The outer diameter of the catheter tube 24 in the range of the length "La" is made 2 to 50 percent, preferably 2 to 20 percent larger than the outer diameter of the other portion of the catheter tube 24. This range of percent is set because when less than 2 percent, the effect of the hemostatic function is slight, while if over 50 percent, it becomes difficult to insert this into the skin and tissue of the patient, and its fabrication becomes difficult.

In this embodiment, the peel off type cannula shown in FIG. 3D is not necessarily used.

Second Embodiment

Next, a second embodiment of the present invention will be explained. Members in the balloon catheter 20a of the second embodiment shown in FIG. 6 the same as in the first embodiment are given the same references and explanations thereof are omitted.

Figure 6:
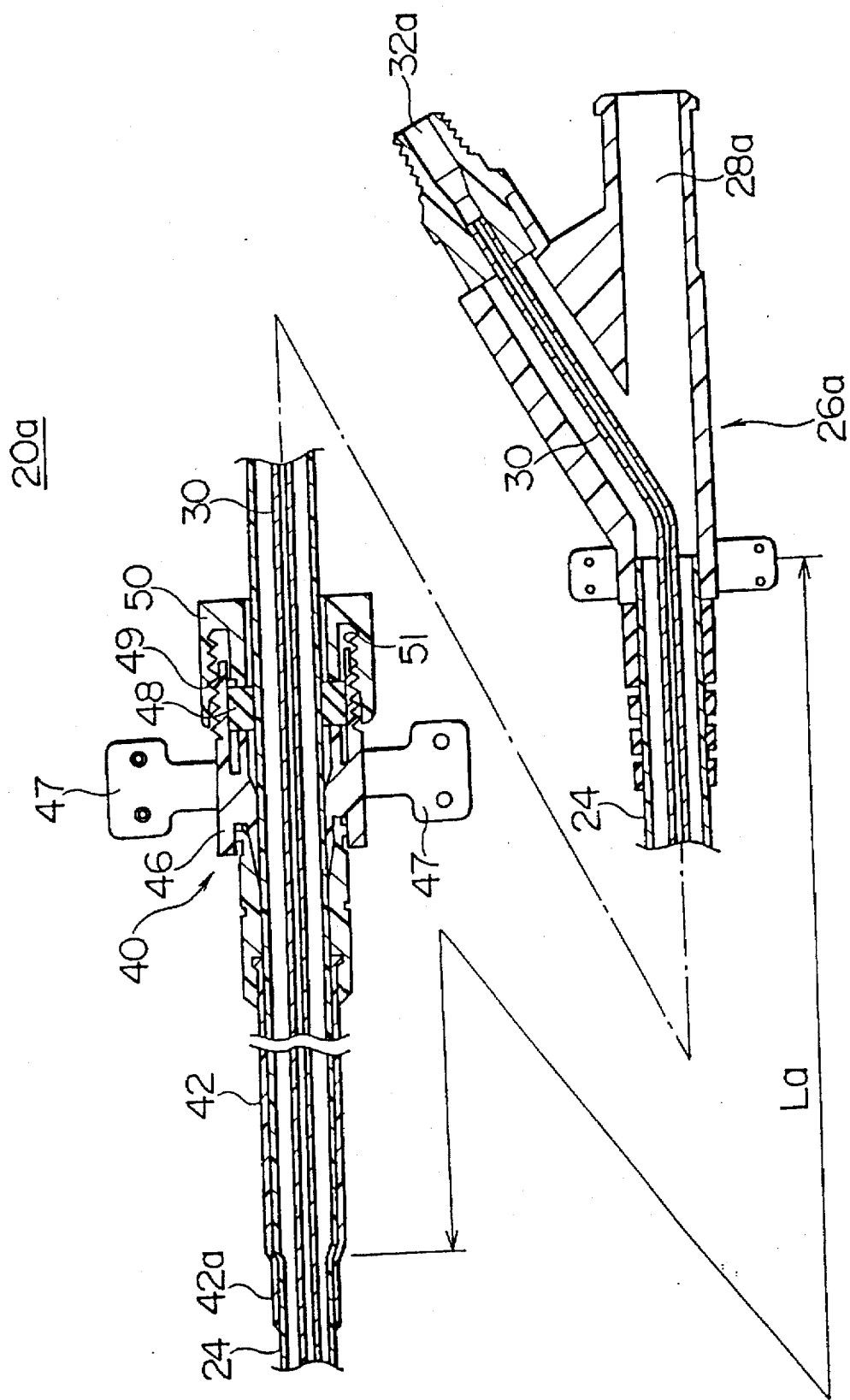
FIG. 6 is a schematic cross-sectional view of a balloon catheter according to a second embodiment of the present invention.

In this embodiment, as shown in FIG. 6, the shuttle gas port 28a formed in the connector 26a is disposed straight along the direction of the axial center of the catheter tube 2awhile the blood pressure measurement port 32a is disposed at a predetermined angle with respect to the axial center of the shuttle gas port 28a. In this embodiment, the channel resistance of the shuttle gas can be expected to be improved by a further 2 percent and the response by a further 4 percent compared with the embodiment shown in FIG. 1, where the blood pressure measurement port 32 is disposed straight along the direction of the axial center of the catheter tube 24. In terms of the flow in the tube, the channel resistance is smaller in the case of a straight flow rather than a curved flow.

Third Embodiment

Next, a third embodiment of the present invention will be explained.

Figure 7:
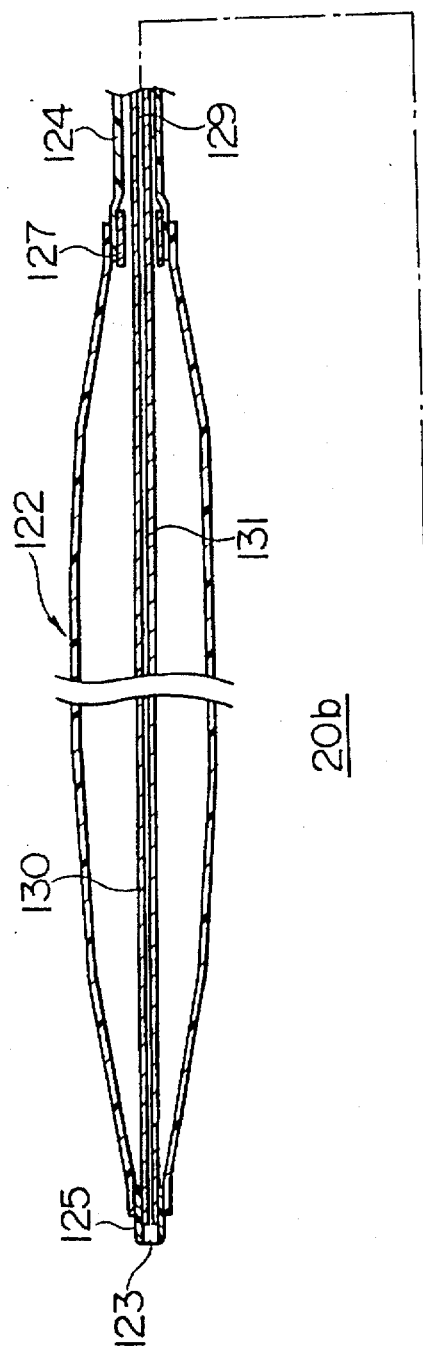
FIG. 7 is a schematic cross-sectional view of a balloon catheter according to a third embodiment of the present invention
Figure 7:
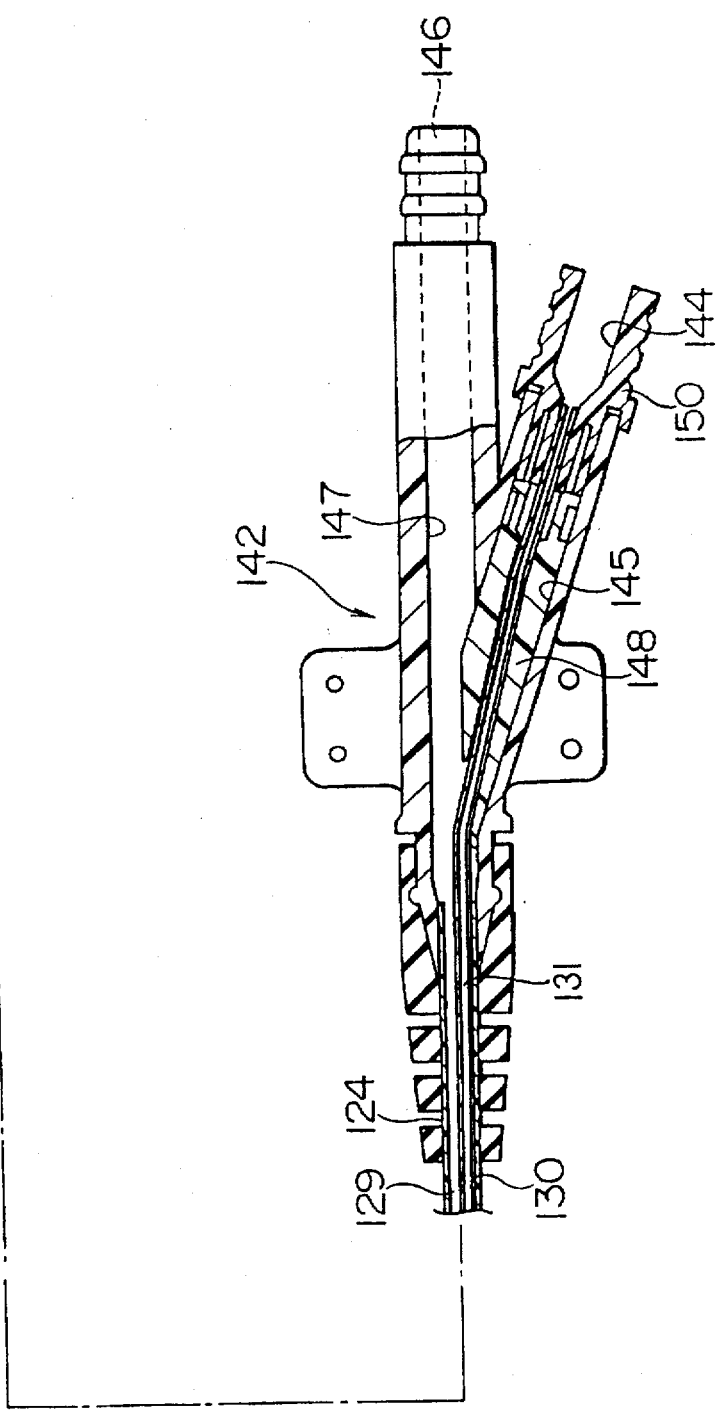

As shown in FIG. 7, the balloon catheter 20b according to the third embodiment of the present invention has a balloon portion 122 which expands and contracts in accordance with the heart beating. The balloon portion 122 is comprised of a thin film of a thickness of approximately 100 to 150 µm. The material of the thin film is not particularly limited, but it is preferably a material superior in resistance to flexural fatigue, for example, is comprised of polyurethane. The outer diameter and length of the balloon portion 122 are determined in accordance with the inner volume of the balloon portion 122, which has a great effect on the effect of assisting the heart beatings, the inner diameter of the arterial blood vessel, and the like. The inner volume of the balloon portion 122 is not particularly limited, but may be 30 to 50 cc. The outer diameter of the balloon portion 122 is preferably 14 to 16 mm, and the length is preferably 210 to 270 mm.

At the distal end of the balloon portion 122 there is attached by a means such as heat bonding or adhesion a front tip portion 125 with a blood port 123 formed in it.

At the inner circumference of the front tip portion 125 is attached the distal end of the inner tube 130 by heat bonding or adhesion.

At the proximal end of the balloon portion 122 at the outer circumference of a metal connecting tube 127 is connected the distal end of the catheter tube 124. The fluid pressure is introduced to or released from the inside of the balloon portion 122 through the fluid pressure passage 129 formed in the inside of the catheter tube 124 so as to make the balloon portion 122 expand or contract. The balloon portion 122 and the catheter tube 124 are connected by heat bonding or adhesion by an adhesive such as an ultraviolet ray curable resin.

The inner tube 130 extends in the axial direction inside the balloon portion 122 and the catheter tube 124 and is communicated with the later mentioned blood pressure measurement port 144 of the bifurcation 142. At the inside, there is formed a blood passage 131 which is not communicated with the inside of the balloon portion 122 and the fluid pressure passage 129 formed in the catheter tube 124. The inner tube 130 positioned in the balloon portion 122 is also used as the guide wire insertion cannula at the time of inserting the balloon catheter 20b in the artery. The contracted balloon portion 122 is wound on it for easy insertion of the balloon portion 20b in the artery.

The catheter tube 124 is not particularly limited, but may be comprised of polyurethane, polyvinyl chloride, polyethylene terephthalate, polyamide, etc. The inner diameter and thickness of the catheter tube 124 are not particularly limited, but preferably the inner diameter is 1.5 to 4.0 mm and the thickness is 0.05 to 0.4 mm. Further, the inner tube 130 is not particularly limited, but may be comprised by a hard tube, a metal spring reinforced tube, a fine stainless steel tube, etc. The inner diameter and thickness of the inner tube 130 are not particularly limited, but the inner diameter is preferably 0.1 to 1.0 mm and the thickness is preferably 0.05 to 0.4 mm.

At the proximal end of the catheter tube 124 is connected the bifurcation 142 positioned outside the patient's body. The bifurcation 142 is formed separate from the catheter tube 124 and is affixed by a means such as heat bonding or adhesion. At the bifurcation 142 are formed a first passage 147 formed with a shuttle gas port for introducing or releasing shuttle gas into or out from the inside of the fluid pressure passage 129 in the catheter tube 124 and the balloon portion 122 and a second passage 145 formed with a blood pressure measurement port 144 communicated with the inside of the inner tube.

The shuttle gas port 146 is connected to a driving console 10, for example, as shown in FIG. 5. This driving console 10 is used to introduce or release the fluid pressure in the balloon portion 122.

The blood pressure measurement port 144 is connected for example to a blood pressure measurement apparatus, which can measure the fluctuations in the pressure of the arterial blood taken from the blood port 123 of the distal end of the balloon portion 122. Based on the fluctuations in the blood pressure measured by the blood pressure measurement apparatus, the driving console 10 shown in FIG. 5 is controlled in accordance with the heart beating to make the balloon portion 122 expand or contract.

Figure 8:
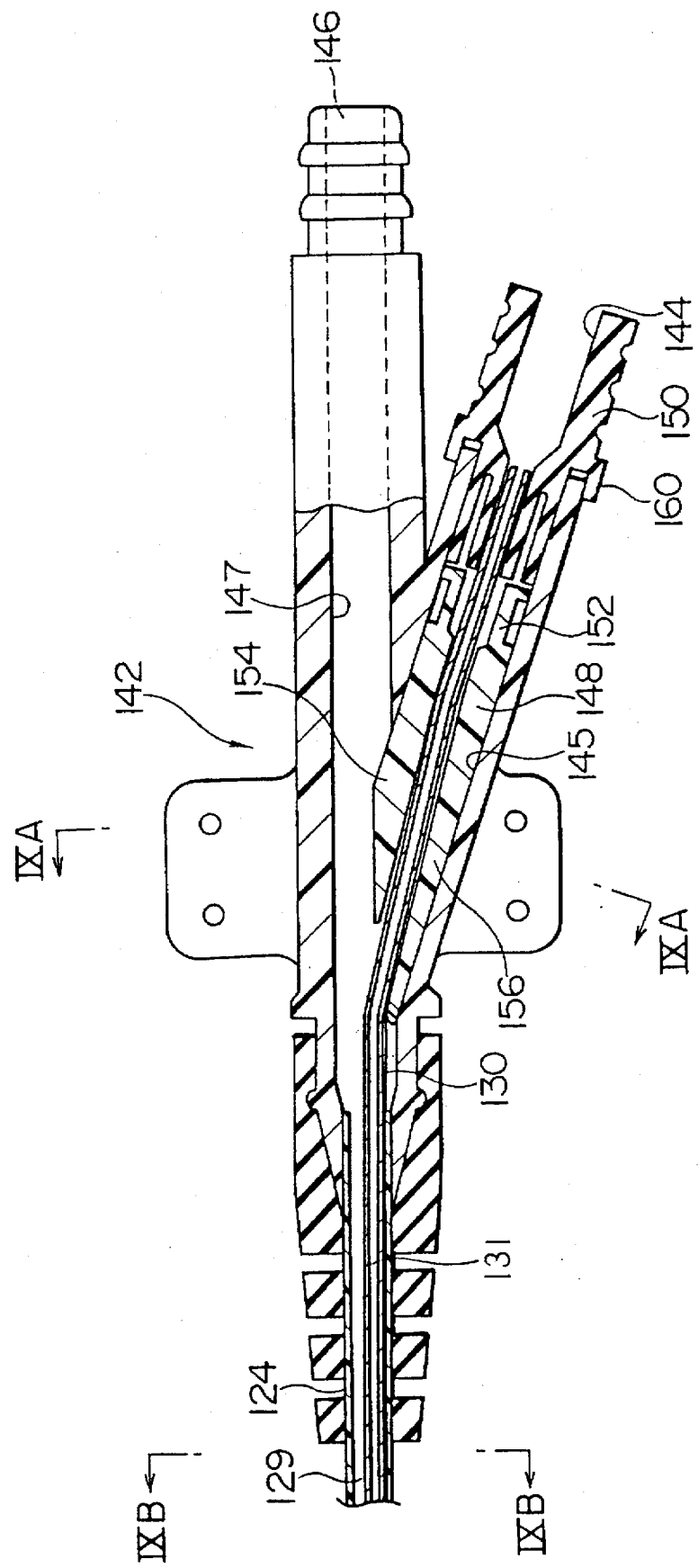
FIG. 8 is an enlarged cross-sectional view of key portions of the bifurcation shown in FIG. 7.

At the bifurcation 142 of this embodiment, as shown in FIGS. 7 and 8, the first passage 147 formed with the shuttle gas port 146 is disposed straight along the direction of the axial center of the catheter tube 124, while the second passage 145 formed with the blood pressure measurement port 144 is disposed at a predetermined angle with respect to the axial center of the first passage 147.

Further, in the bifurcation 142 of the embodiment, the second passage 145 has attached in it a first inner tube end holder 148 and a second inner tube end holder 150 for making the inner tube 130 be disposed eccentrically so as to contact the inner wall of the catheter tube 124.

Figure 11A:
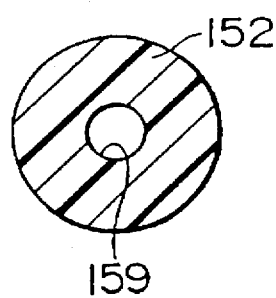
FIGS. 11A to 11C are cross-sectional views taken along the lines XIA—XIA, XIB—XIB, and XIC—XIC shown in FIG. 10.
Figure 11B:
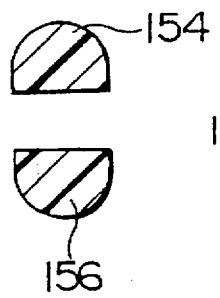
Figure 11C:
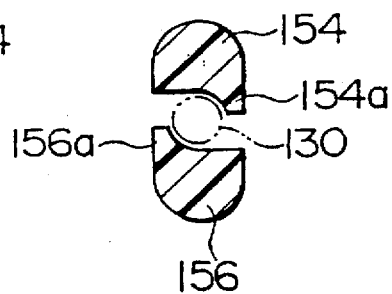

The first inner tube end holder 148, as shown in FIGS. 10 and 11A to 11C, has a holder body 152 and a pair of claws 154 and 156 which project out in the axial direction with respect to the holder body 152. In the holder body 152 are formed a free insertion site 158 in which the end of the inner tube 130 is loosely inserted and an adhesion insertion site 159 for adhering the outer circumference of the inner tube 130 to the body 152. The claws 154 and 156 are comprised to grip the end of the inner tube 130. At the base end side, as shown in FIG. 11B, they have a substantially semicircular shape, while at their distal ends, as shown in FIG. 11C, they have shapes with projections 154a and 156a so as to grip the two sides of the inner tube 130.

The other lower claw 156 is made longer than the other upper claw 154. As shown in FIGS. 7 and 8, when the first inner tube end holder 148 is inserted into the second passage 145 of the bifurcation 142, the first passage 147 is prevented from being narrowed much by the distal ends of the claws 154 and 156.

Figure 9A:
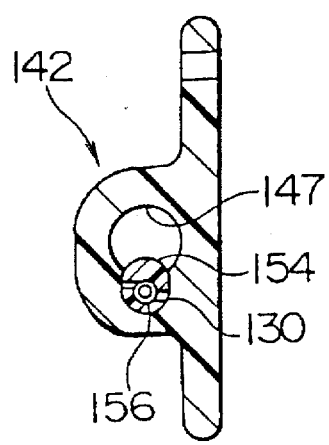
FIGS. 9A and 9B are cross-sectional views taken along the lines IXA—IXA and IXB—IXB shown in FIG. 8.
Figure 9B:
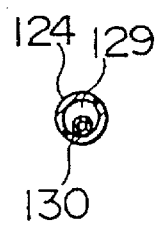
Figure 10:
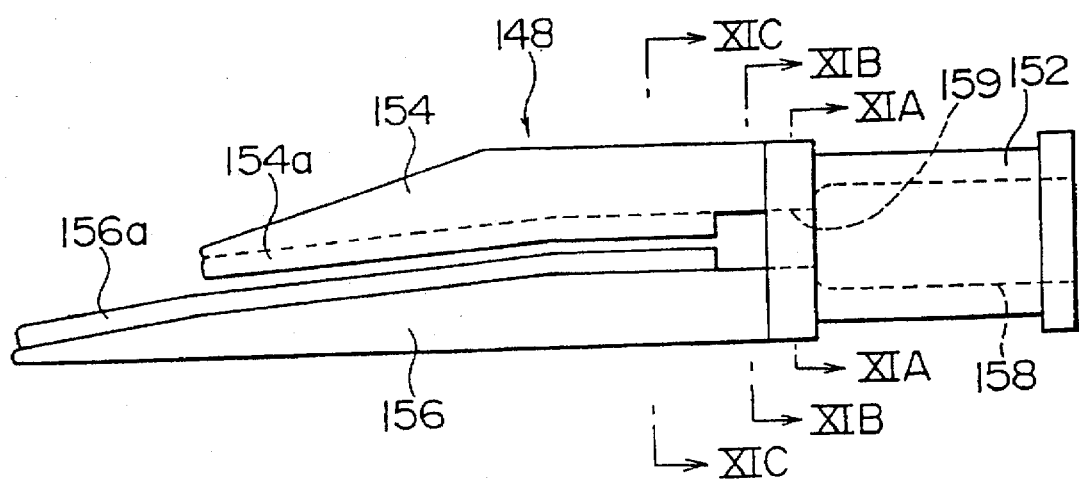
FIG. 10 is a side view of a first inner tube end holder shown in FIG. 8.

Using these claws 154 and 156, it is possible to flexibly hold the end of the inner tube 130. Further, these claws 154 and 156 flexibly hold the end of the inner tube 130 as shown in FIG. 9A. The inner tube 130, as shown in FIG. 9B, is thereby disposed eccentrically so as to contact the inner wall of the catheter tube 124.

Figure 12:
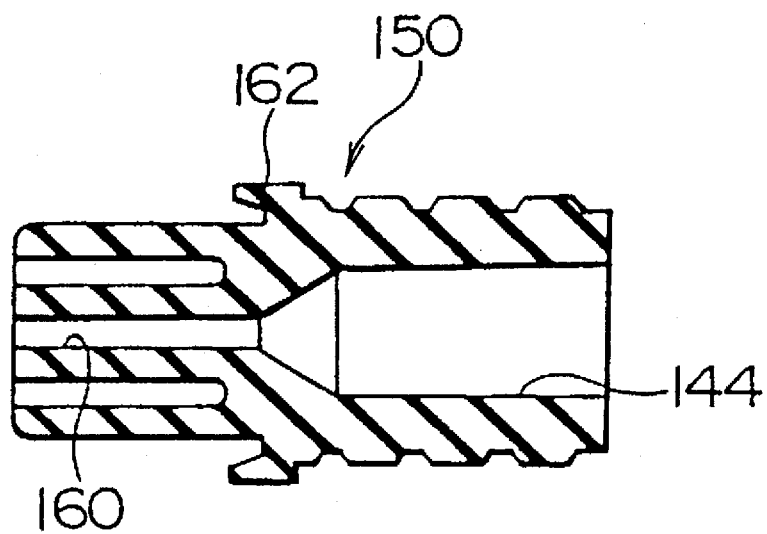
FIG. 12 is a cross-sectional view of a second inner tube end holder shown in FIG. 8.

Inside the second passage 145 of the proximal end side of the first inner tube end holder 148 is attached a second inner tube end holder 150. In this second inner tube end holder 150, as shown in FIG. 12, are formed an end fixing hole 160 in which the end of the inner tube 130 is flexibly inserted and a blood pressure measurement port 144 communicated with the inside of the inner tube 130. The second inner tube end holder 150 is engaged with the bifurcation 142 by an engagement projection 162 formed on its outer circumference.

To affix the end of the inner tube 130 in the second passage 145 of the bifurcation 142 by the first and second inner tube end holders 148 and 150, first the end of the inner tube 130 is passed through the second passage 145 of the bifurcation 142 and is drawn out to the outside of the bifurcation 142 from the passage 145. Next, the first inner tube end holder 148 is inserted into the second passage 145 and the end of the inner tube 130 is elastically held between the claws 154 and 156. Further, the end of the inner tube 130 is pulled and the inner tube 130 is disposed to be eccentric so as to contact the inner wall of the catheter tube 124, as shown in FIG. 9B. After this, the end of the inner tube 130 is cut to a suitable length and the end of the inner tube 130 is adhered to the first inner tube end holder 148. Next, the second inner tube end holder 150 is inserted into the first passage 145 and the end of the inner tube 130 is affixed to the end fixing hole 160 of the holder 150.

In the balloon catheter 20b of this embodiment, the first passage 147 communicating with the shuttle gas port 146 formed in the bifurcation 142 is disposed straight along the direction of the axial center of the catheter tube 124, so the channel resistance of the shuttle gas is improved 2 percent and the response is improved 4 percent compared with the prior art where the blood pressure measurement port was disposed straight along the direction of the axial center of the catheter tube.

Further, in this embodiment, since the first inner tube end holder 148 is attached to the second passage 145 of the bifurcation 142, the inner tube 130 is disposed eccentrically to contact the inner wall of the catheter tube 124. As a result, the channel resistance of the fluid pressure passage 129 formed in the catheter tube 124 can be reduced 4 percent compared with the conventional catheter and the response can be improved 8 percent. In the past, when snaking the catheter tube 124 along the blood vessel, the inner tube 130 was snaked relatively inside the catheter tube 124 and the channel resistance of the fluid pressure passage 129 was increased. But in this embodiment, the inner tube 130 is disposed eccentrically so as to contact the inner wall of the catheter tube 124, so the channel resistance of the fluid pressure passage 129 is reduced.

In this embodiment, further, the first inner tube end holder 148 and the second inner tube end holder 150 were formed separately, but these may also be formed integrally. Further, the specific shapes and constructions of the first inner tube end holder 148 and second inner tube end holder 150 can be modified in various ways within the scope of the present invention.

Fourth Embodiment

Next, a fourth embodiment of the present invention will be explained.

Figure 13:
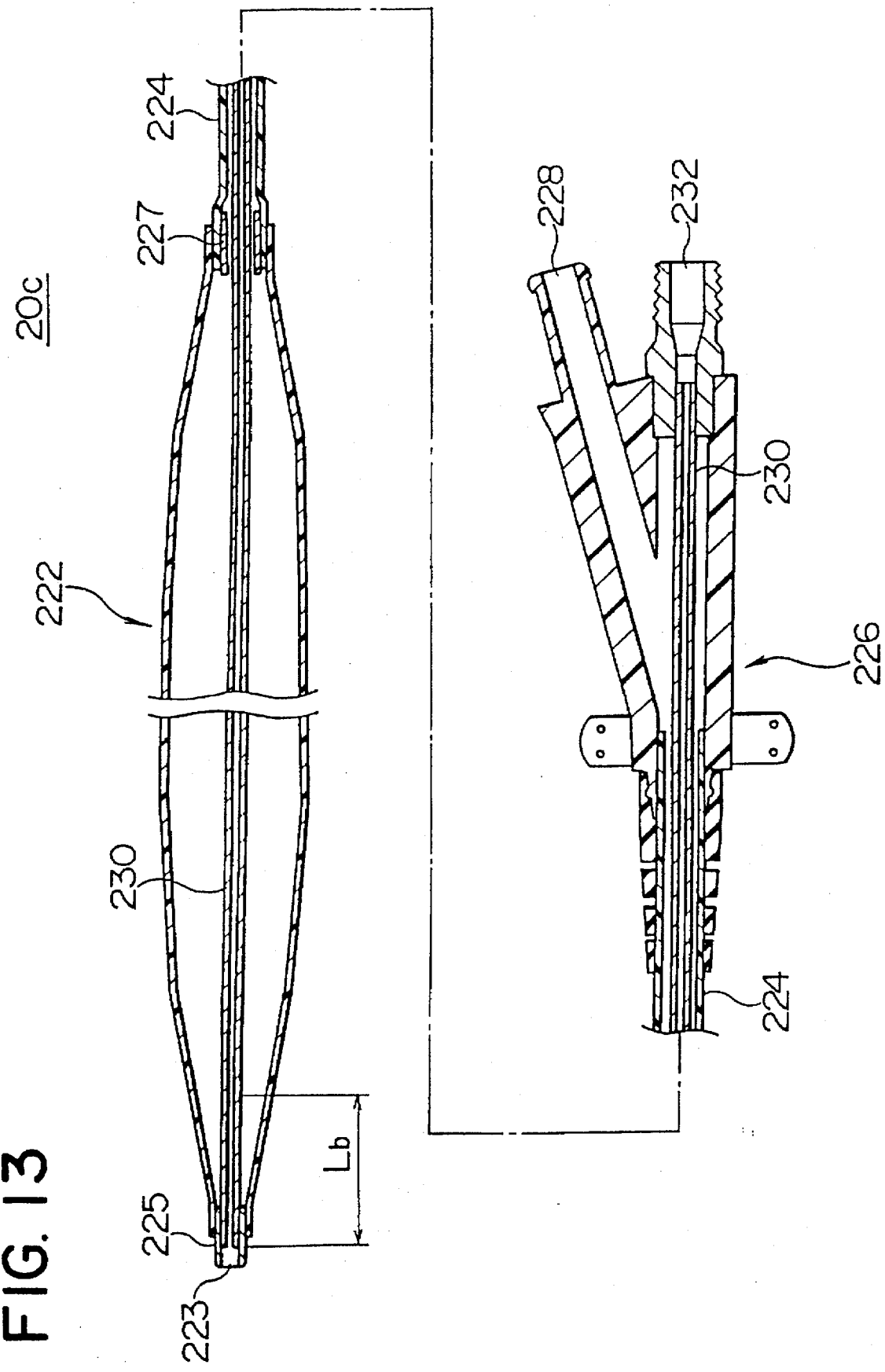
FIG. 13 is a schematic cross-sectional view of a balloon catheter according to a fourth embodiment of the present invention.

As shown in FIG. 13, the balloon catheter 20c according to the fourth embodiment of the present invention has a balloon portion 222 which expands and contracts in accordance with the heart beating. The balloon portion 222 is comprised by a thin film of a thickness of about 100 to 150 μm. The material of the thin film is not particularly limited, but preferably is a material superior in resistance to flexural fatigue, for example, is made of polyurethane. The outer diameter and length of the balloon portion 222 are determined in accordance with the inner volume of the balloon portion 222, which greatly affects the heat function assisting action, the inner diameter of the arterial blood vessel, etc. The inner volume of the balloon portion 222 is not particularly limited, but may be 30 to 50 cc. The outer diameter of the balloon portion 222 is preferably from 14 to 16 mm, and the length in the axial direction is preferably 210 to 270 mm.

At the distal end of the balloon portion 222, a front tip portion 225 formed with a blood port 223 is attached by means of heat bonding, adhesion, etc.

At the inner circumference side of the front tip portion 225 is attached the distal end of the inner tube 230 by a means such as heat bonding or adhesion.

The inner tube 230 extends in the balloon portion 222 and the catheter tube 224 in the axial direction and communicates with the blood pressure measurement port 232 of the bifurcation 226 mentioned later. Its inside is not communicated with the inside of the balloon portion 222.

The inner tube 230 positioned in the balloon portion 222 also acts as a guide rod at the time of inserting the balloon catheter 20c in the artery. The contracted balloon portion 222 is wound on it so that the balloon portion 222 can be inserted easily into the artery.

At the proximal end of the balloon portion 222 is connected the distal end of the catheter tube 224 at the outer circumference side of the metal connecting tube 227. The fluid pressure is introduced into or released from the inside of the balloon portion 222 through the catheter tube 224 so as to make the balloon portion 222 expand or contract. The balloon portion 222 and the catheter tube 224 are connected by heat bonding or adhesion by an adhesive such as an ultraviolet ray curable resin.

The material comprising the catheter tube 224 is not particularly limited, and use may be made of polyurethane, polyvinyl chloride, polyethylene, nylon, etc. Further, the inner diameter and thickness of the catheter tube 224 are not particularly limited. The inner diameter, however is preferably 1.5 to 4.0 mm and the thickness is preferably 0.05 to 0.4 mm.

At the proximal end of the catheter tube 224 is connected the bifurcation 226 set outside the patient's body. The bifurcation 226 may be formed separately from the catheter tube 224 and be affixed by a means such as heat bonding or adhesion, but may also be formed integrally with the catheter tube 224. In the bifurcation 226 are formed a shuttle gas port 228 for introducing or releasing shuttle gas to or from the catheter tube 224 and balloon portion 222 and a blood pressure measurement port 232 communicated with the inside of the inner tube 230.

The shuttle gas port 228 is connected to the driving console 10 shown in FIG. 5. This driving console 10 is used to introduce or release the fluid pressure in the balloon portion 222.

The blood pressure measurement port 232 is connected, for example, to a blood pressure measurement apparatus so as to enable measurement of the fluctuations in the pressure of the arterial blood taken from the blood port 232. The heart beating is detected based on the fluctuations in the blood pressure measured by the blood pressure measurement apparatus and the driving console 10 shown in FIG. 5 is controlled in accordance with the heart beating so as to make the balloon portion 222 expand or contract.

In this embodiment, the inner tube 230 is comprised of a metal tube. The metal constituting the inner tube 230 is not particularly limited, but stainless steel or tungsten may be used and stainless steel is preferably used. In particular, in this embodiment, the distal end portion "Lb" of the inner tube 230 is preferably set to a low hardness by heat treatment. When the hardness of the portions other than the distal end portion "Lb" of the inner tube 230 is 100 percent, the distal end portion "Lb" is preferably set to a hardness of 10 to 60 percent. If under 10 percent, it is too soft, which is undesirable, while if over 60 percent, there is little effect as a guide at the time of insertion of the balloon catheter. For example, when a stainless steel tube is used as the inner tube 230, the Vicker's hardness is about 350so the distal end of the stainless steel tube can be heat treated by annealing at 800° to 1000° C. to reduce the Vicker's hardness to 150 to 250 or so. As a result, just the distal end "Lb" of the inner tube 230 is improved in flexibility compared with the other portions and, when inserting the balloon catheter 20c in the blood vessel, easy insertion in a snaking blood vessel is possible without damaging the inner walls of the blood vessel.

The range of the distal end "Lb" improved in flexibility by heat treatment or other means described later is preferably 3 to 15 cm. The inner diameter and thickness of the inner tube 230 are not particularly limited, but the inner diameter is preferably 0.1 to 1.0 mm and the thickness is preferably 0.05 to 0.4 min.

Figure 14:
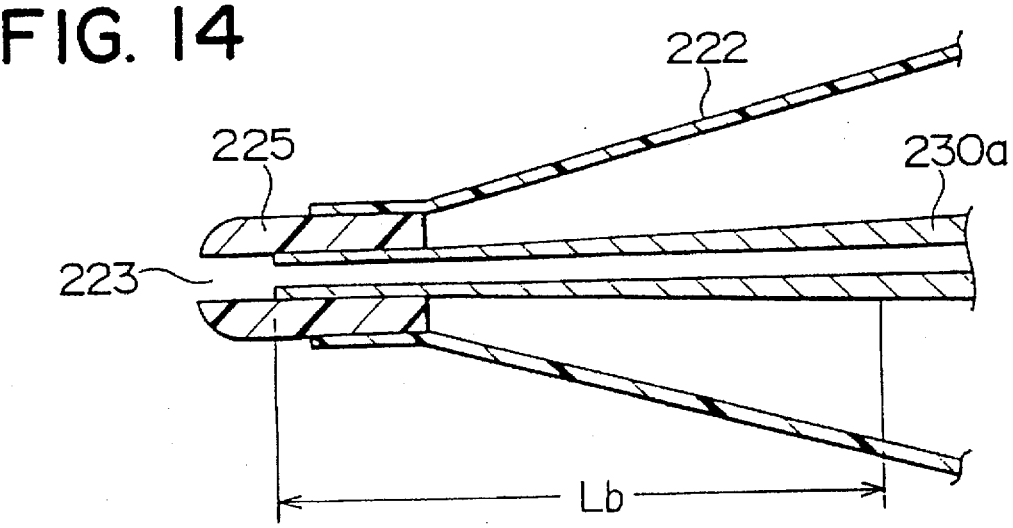
FIG. 14 is a cross-sectional view of key portions of the inner tube distal end showing a modification of the embodiment shown in FIG. 13.

In the embodiment shown in FIG. 14, a taper is given to the distal end portion "Lb" of the inner tube 230a and the thickness of the distal end portion is formed smaller than other portions. For example, when the thickness of the inner tube 230a at portions other than the distal end portion "Lb" is 100 percent, the thickness of the distal end portion is preferably set to 30 to 70 percent. Specifically, when the thickness of the inner tube 230a at portions other than the distal end portion "Lb" is made 80 µm, the distal end portion "Lb" is set thin so that the tapered distal end portion becomes 50 µm or so. The means for setting just the distal end portion "Lb" thinner in this way is not limited to chemical polishing, electropolishing, and machine polishing. Other means may be used as well. When performing chemical polishing, just the distal end portion "Lb" of the inner tube 230a is immersed in an etching solution of nitric acid etc. and then the inner tube 230a is lifted out at a fixed speed.

With this embodiment as well, it is possible to increase the flexibility of only the distal end portion "Lb" of the inner tube 230a l compared with the other portions.

Figure 15:
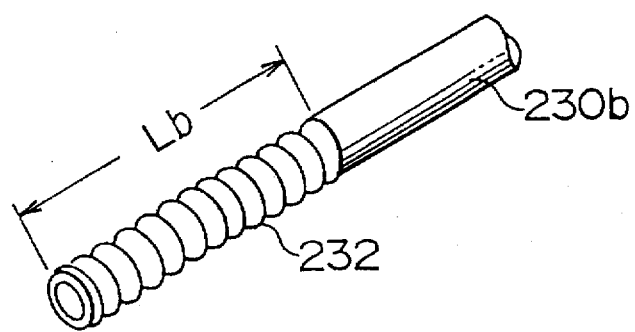
FIG. 15 is a perspective view of key portions of the inner tube distal end showing another modification of the embodiment shown in FIG. 13.

In the embodiment shown in FIG. 15, a bellows-like irregularity 232 is formed at the outer circumference of the distal end portion "Lb" of the inner tube 230b. This bellows-like irregularity 232 may be a simple bellows-like irregularity with independent sections in the axial direction or a spiral bellows-like irregularity.

Figure 16:
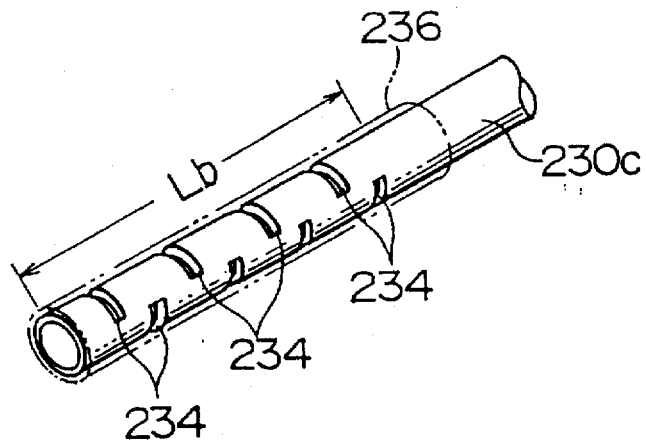
FIG. 16 is a perspective view of key portions of the inner tube distal end showing still another modification of the embodiment shown in FIG. 13.

Further, in the embodiment shown in FIG. 16, different slits 234 are formed in the distal end portion "Lb" of the inner tube 230c. In this embodiment, the inner circumference and outer circumference of the inner tube 230c may be communicated by the slits 234, so it is preferable to cover the outer circumference of the distal end portion "Lb" with a thin polymer coating 236. As the polymer coating 236, one of polyurethane or nylon is preferable.

In the embodiment shown in FIGS. 15 and 16 too, it is possible to increase the flexibility of the distal end portion "Lb" of the inner tube 230b and 230cso a similar action and effect are exhibited as with the embodiment shown in FIGS. 13 and 14.

Note that in the present invention, use may also be made of a combination of the above embodiments. For example, the embodiment shown in FIG. 13 and the embodiment shown in FIG. 14 may be combined and the distal end portion of the inner tube heated treated and chemically polished so as to increase the flexibility of the distal end portion "Lb". Further, the embodiment shown in FIG. 13 and the embodiment shown in FIG. 15 or 16 may be combined and the distal end portion of the inner tube heated treated and also given a bellows-like irregularity or slits so as to increase the flexibility of the distal end portion "Lb". Other combinations are also conceivable.

Fifth Embodiment

Next, a fifth embodiment of the present invention will be explained.

Figure 17:
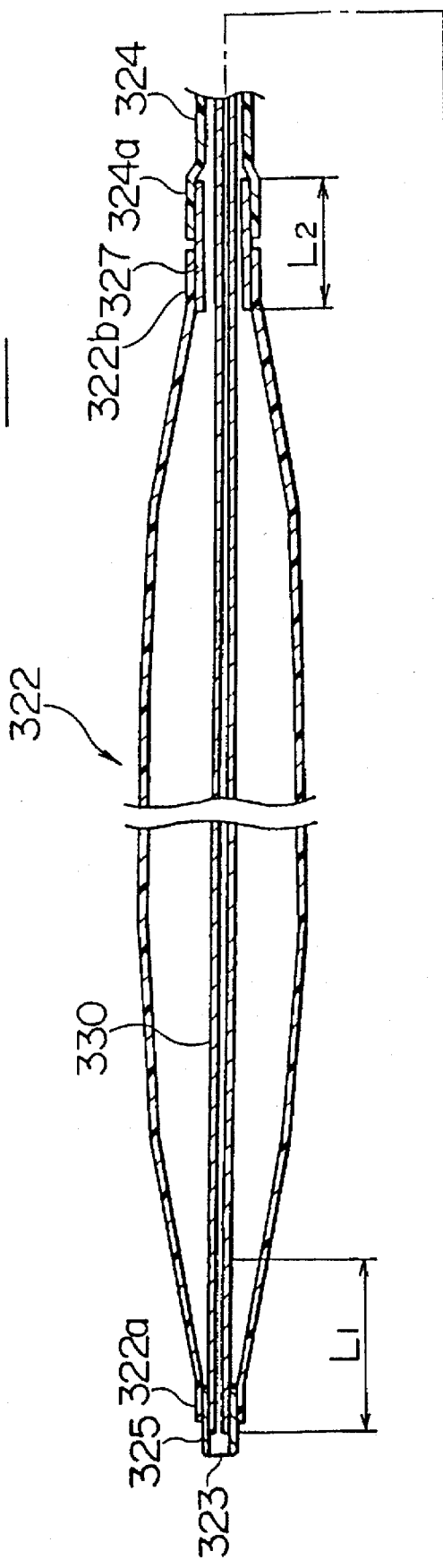
FIG. 17 is a schematic cross-sectional view of a balloon catheter according to a fifth embodiment of the present invention.
Figure 17:
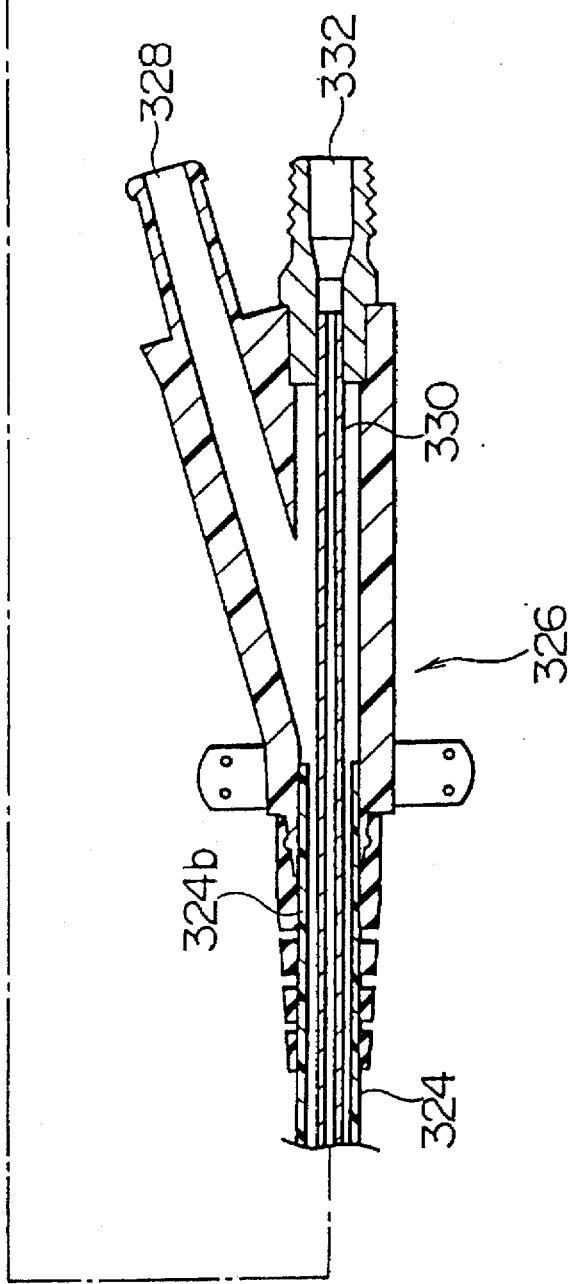

As shown in FIG. 17, the balloon catheter 20d of the fifth embodiment of the present invention has a balloon portion 322 which expands and contracts in accordance with the heart beating. The balloon portion 322 is comprised of a thin film of a thickness of 100 to 150 μm or so. The material of the thin film is not particularly limited, but preferably it is a material superior in resistance to flexural fatigue, for example, is made of polyurethane. The outer diameter and length of the balloon portion 320 are determined in accordance with the inner volume of the balloon portion 320, which has a large influence on the effect of assistance of the heart beatings, the inner diameter of the arterial blood vessel, etc. The inner volume of the balloon portion 320 is not particularly limited, but is preferably 30 to 50 cc. The outer diameter of the balloon portion 320 at the time of expansion is preferably 14 to 16 mm, while the length in the axial direction is preferably 210 to 270 mm.

At the distal end 322a of the balloon portion 322 is attached a front tip portion 325 formed with a blood port 323 by a means such as heat bonding or adhesion. The front tip portion 325 is for example comprised of plastic, but preferably has a contrast medium etc. mixed in to enable a contrast when X-rayed.

At the inner circumference side of the front tip portion 325, the distal end of the inner tube 330 is attached by a means such as heat bonding or adhesion.

The inner tube 330 extends in the balloon portion 322 and the catheter tube 324 in the axial direction and communicates with the blood pressure measurement port 332 of the bifurcation 326 mentioned later. The inside is not communicated with the inside of the balloon portion 322.

The inner tube 330 is for example comprised of a plastic tube reinforced by a mesh etc. or a metal tube. The metal constituting the inner tube 330 is not particularly limited, but may be stainless steel and tungsten. Preferably, stainless steel is used.

When using a metal tube for the inner tube 330, the distal end portion $L_1$ of the inner tube 330 at the blood port side is preferably set to a low hardness by heat treatment. When the hardness of the portions other than the distal end portion $L_1$ of the inner tube 330 is 100 percent, the distal end portion $L_1$ is preferably set to a hardness of 10 to 60 percent. If under 10 percent, it is too soft, which is undesirable, while if over 60 percent, there is little effect as a guide at the time of insertion of the balloon catheter. For example, when a stainless steel tube is used as the inner tube 330, the Vicker's hardness is about 350 so the distal end of the stainless steel tube can be heat treated by annealing at 800° to 1000°C. to reduce the Vicker's hardness to 150 to 250 or so. As a result, just the distal end of the inner tube 330 is improved in flexibility compared with the other portions and, when inserting the balloon catheter 20d in the blood vessel, easy insertion in a snaking blood vessel is possible without damaging the inner walls of the blood vessel.

As a means for increasing the flexibility of the distal end portion of the metal inner tube 330, in addition to the means of reducing the hardness by heat treatment, use may be made of any one or any combination of the means of reducing the thickness of the distal end portion, the means of forming a bellows-like irregularity at the distal end portion, and the means of providing slits in the distal end portion. The range of the distal end portion is preferably from 3 to 15 cm.

In this embodiment, the proximal end 322b of the balloon portion 322 is joined to the outer circumference of one end of the metal connection tube 327. At the outer circumference of the other end of the connection tube 327 is joined the distal end 324a of the catheter tube 324. As a result, unlike in the prior art, the proximal end 322b of the balloon portion 322 and the distal end 324a of the catheter tube 324 are not superposed at the outer circumference of the connection tube 327. The balloon portion 322 and the catheter tube 324 are connected through the connection tube 327 and communicated inside. Therefore, the fluid pressure is introduced to or released from the inside of the balloon portion 322 through the catheter tube 324 to make the balloon portion 322 expand or contract.

The connection tube 327 is not particularly limited and for example may be comprised of a metal such as stainless steel or tungsten. The outer diameter is preferably 1.5 to 4 mm and the thickness is preferably 30 to 150 μm. Further, the length $L_2$ is preferably 8 to 30 mm. If the length $L_2$ of the connection tube 327 is too long, the flexibility of the catheter as a whole drops and the insertability is affected, so this is not desirable. If too short, there is a tendency for the join to be insufficient, so this is also not desirable.

In this embodiment, the connection tube 327 is comprised of metal so as to partition off the balloon portion and the catheter tube at the connection tube and facilitate the expansion and contraction of the balloon portion and so as to enable the position of the proximal end of the balloon portion to be confirmed during image formation by X-rays etc. Also, comparing a metal tube and plastic tube, a metal tube can be made smaller in thickness under conditions of the same outer diameter and same rigidity. If the thickness can be reduced, the channel cross-section becomes wider and the response of the expansion and contraction becomes better.

As the means for joining the proximal end 322b of the balloon portion or the distal end 324a of the catheter tube with the connection tube 327, use may be made of the means of heat bonding, adhesion by an adhesive, etc. In the case of using adhesion, as the primer, use is preferably made of an epoxy resin, polyimide resin, etc. superior in bonding with metal. The primer is preferably coated thinly to about 10 μm, for example, on the outer circumference of the connection tube 327. Further, the outer circumference of the connection tube 327 may be treated to roughen it to improve the bonding ability.

The material comprising the catheter tube 324 is not particularly limited, but use may be made of polyurethane, polyvinyl chloride, polyethylene, nylon, etc. Further, the inner diameter and thickness of the catheter tube 324 are not particularly limited, but preferably the inner diameter is 1.5 to 4.0 mm and the thickness is 150 to 300 μm.

The bifurcation 326 set outside the patient's body is connected to the proximal end 324b of the catheter tube 324. The bifurcation 326 may be formed separate from the catheter tube 324 and be affixed by means such as heat bonding or adhesion and may also be formed integrally with the catheter tube 324. At the bifurcation 326 are formed a shuttle gas port 328 for introducing or releasing the shuttle gas into or from the inside of the catheter tube 324 and balloon portion 322 and a blood pressure measurement port 332 communicated with the inside of the inner tube 330.

The shuttle gas port 328 is connected to the driving console 10 shown in FIG. 5. Due to this driving console 10, the fluid pressure is introduced to or released from the inside of the balloon portion 322.

The blood pressure measurement port 332 is connected for example to a blood pressure measurement apparatus so as to enable measurement of the fluctuations in the pressure of the arterial blood taken from the blood port 323. The heart beating is detected based on the fluctuations in the blood pressure measured by the blood pressure measurement apparatus. The driving console 10 shown in FIG. 5 is controlled in accordance with the heart beating to make the balloon portion 322 expand or contract.

Note that the present invention is not limited to the above embodiments. Various modifications are possible within the scope of the invention.

For example, the inner tubes 30, 130, 230, and 330 are not limited to use for measurement of the blood pressure. They may be used for other applications as well.

Further, in the above embodiments, the balloon catheters had inner tubes 30, 130, 230, and 330 inside them, but these inner tubes are not necessarily required. The present invention can also be applied to a balloon catheter having a simple stem rod etc. The present invention can be applied to all types of balloon catheters.

[Examples]

Next, the present invention will be explained with reference to specific examples.

Example 1

As the inner tube 131 shown in FIG. 7, use was made of a fine nylon tube of an outer diameter of 1.4 mm and a thickness of 200 µm. As the thin film comprising the balloon portion 122, use was made of a polyurethane film of a thickness of 0.1 mm. The outer diameter of the balloon portion when expanded was 15 mm, the inner volume of the balloon portion was 30 cc, and the length in the axial direction was 230 mm. As the catheter tube 124, use was made of a polyurethane tube of a length of 550 mm. The outer diameter was 3.0 mm and the thickness was 250 µmm.

As the bifurcation 142, use was made of a bifurcation 142 having the first inner tube end holder 148 and the second inner tube end holder 150 shown in FIGS. 7 to 12. It was confirmed that the inner tube 130 was disposed in the catheter tube 124 in an eccentric manner contacting the inner wall of the catheter tube 124.

The balloon catheter was passed into an acrylic simulated blood vessel of an inner diameter of 60 mm and a length of 350 mm so as to investigate the channel resistance of the fluid pressure passage of the catheter tube (pressure loss) and the response (maximum number of beats). The results are shown in Table 1. Note that in Table 1the maximum number of beats shows the maximum number of beats of full opening and closing of the balloon. The larger the value, the better the response.

TABLE 1

|  | Pressure loss at time of balloon expansion (mmHg) | Pressure loss at time of balloon contraction (mmHg) | Maximum number of beats (beats/min) |
| --- | --- | --- | --- |
| Ex. 1 | 141 | 129 | 110 |
| Ex. 2 | 146 | 132 | 106 |

TABLE 1-continued

|  | Pressure loss at time of balloon expansion (mmHg) | Pressure loss at time of balloon contraction (mmHg) | Maximum number of beats (beats/min) |
| --- | --- | --- | --- |
| Comp. Ex. 1 | 150 | 135 | 102 |

Example 2

A balloon catheter was prepared similar to that of Example 1 except that there were no first inner tube end holder 148 and second inner tube end holder 150 and the inner tube 130 was not disposed eccentrically inside the catheter tube 124. This balloon catheter was used to find the pressure loss and the maximum number of beats in the same way as in Example 1. The results are shown in Table 1.

Comparative Example 1

A balloon catheter was prepared similar to that of Example 1 except that it had a conventional bifurcation and had a conventional inner tube which was disposed not in an eccentric manner in a catheter tube. The inner tube was able to move freely in the radial direction of the catheter. The blood pressure measurement port of the conventional bifurcation was disposed straight along the direction of the catheter tube.

This conventional balloon catheter was used to find the pressure loss and the maximum number of beats in the same way as in Example 1. The results are shown in Table 1.

Evaluation

As shown in Table 1the balloon catheters of Examples 1 and 2 had less of a pressure loss, a greater maximum number of beats, and an improved response compared with the comparative example.

Example 3

As the catheter tube 24 shown in FIG. 1, a polyurethane tube of an outer diameter of 3 mm and a thickness of 180 µm was prepared. At the outer circumference of the catheter tube 24, the hemostatic valve 40 shown in FIG. 2 was attached. As the fixed ring 48 used for this hemostatic valve 40, use was made of a rubber tube of an outer diameter of 6.8 mm, an inner diameter of 3.2 mm, and a length in the axial direction of 10 mm. The hardness of the rubber tube was 55 by JIS hardness.

The hemostatic valve 40 was attached to the catheter tube 24 and the cap portion 50 was screwed to the hemostatic valve body 46 so that the fixed ring 48 was compressed. The relationship with the number of screw turns, the change in the inner diameter of the catheter, the change in the catheter holding force, the change in the valve torque, and the change in the pressure resistance was investigated. The results are shown in FIG. 18.

The change in the inner diameter of the catheter shows the degree of crushing of the catheter tube 24. In the figure, this is shown by the curve connecting the diamond marks. The change in the catheter holding force shows the force affixing the catheter tube 24 in the axial direction of the hemostatic valve 40. In the figure, this is shown by the curve connecting the +marks. The change in the valve torque shows the change in the rotational torque of the cap portion 50 screwed on the hemostatic valve body 46. In the figure, this is shown by the curve connecting the square marks. The unit of the vertical axis is kg.cm. The change in pressure resistance shows the change in pressure resistance due to leakage from the clearance between the outer circumference of the catheter tube 24 and the inner circumference of the holding ring 48. In the figure, this is shown by the curve connecting the triangle marks.

Figure 18:
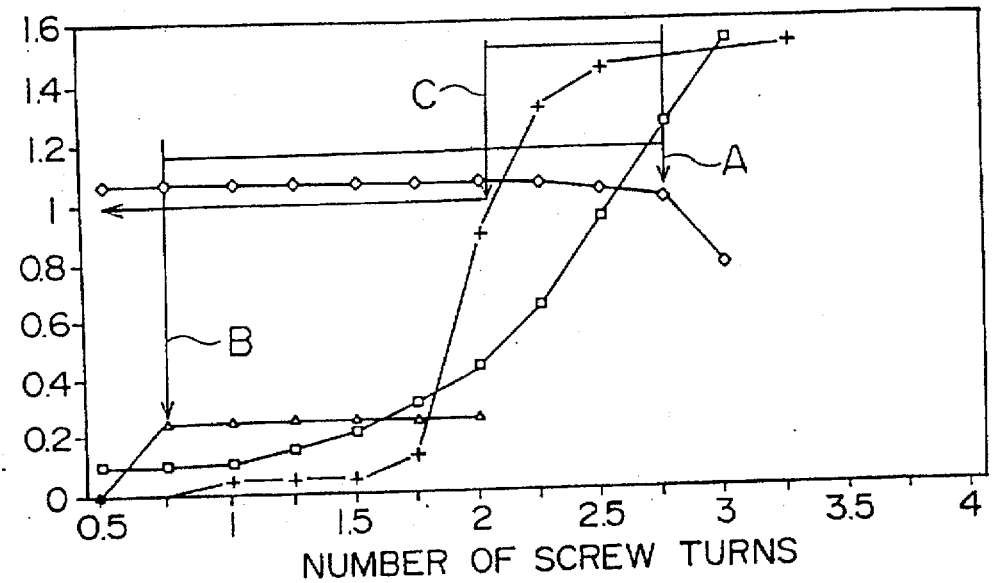
FIG. 18 is a graph showing the characteristic of a hemostatic valve according to an example of the present invention used in a balloon catheter.

As shown in FIG. 18, in the hemostatic valve 40 of the present example, the valve torque rises just before the position A of crushing of the catheter tube 24. This shows that it is difficult to crush the catheter tube 24. Further, at the position B two turns before the position A where the catheter tube 24 is crushed, the pressure resistance rises and a hemostatic action occurs, so the hemostatic action is also excellent. Further, at the position C about one turn before the position A where the catheter tube 24 is crushed, a catheter holding force of over about 1 kg is obtained and the fixing force is good as well.

That is, in the present example, there is a good overall balance among all the functions required for a hemostatic valve.

Example 4

The characteristics of the hemostatic valve were tested in the same way as in Example 3 except that use was made of a rubber tube of a JIS hardness of 72 as the holding ring 48. The results are shown in FIG. 22.

Figure 22:
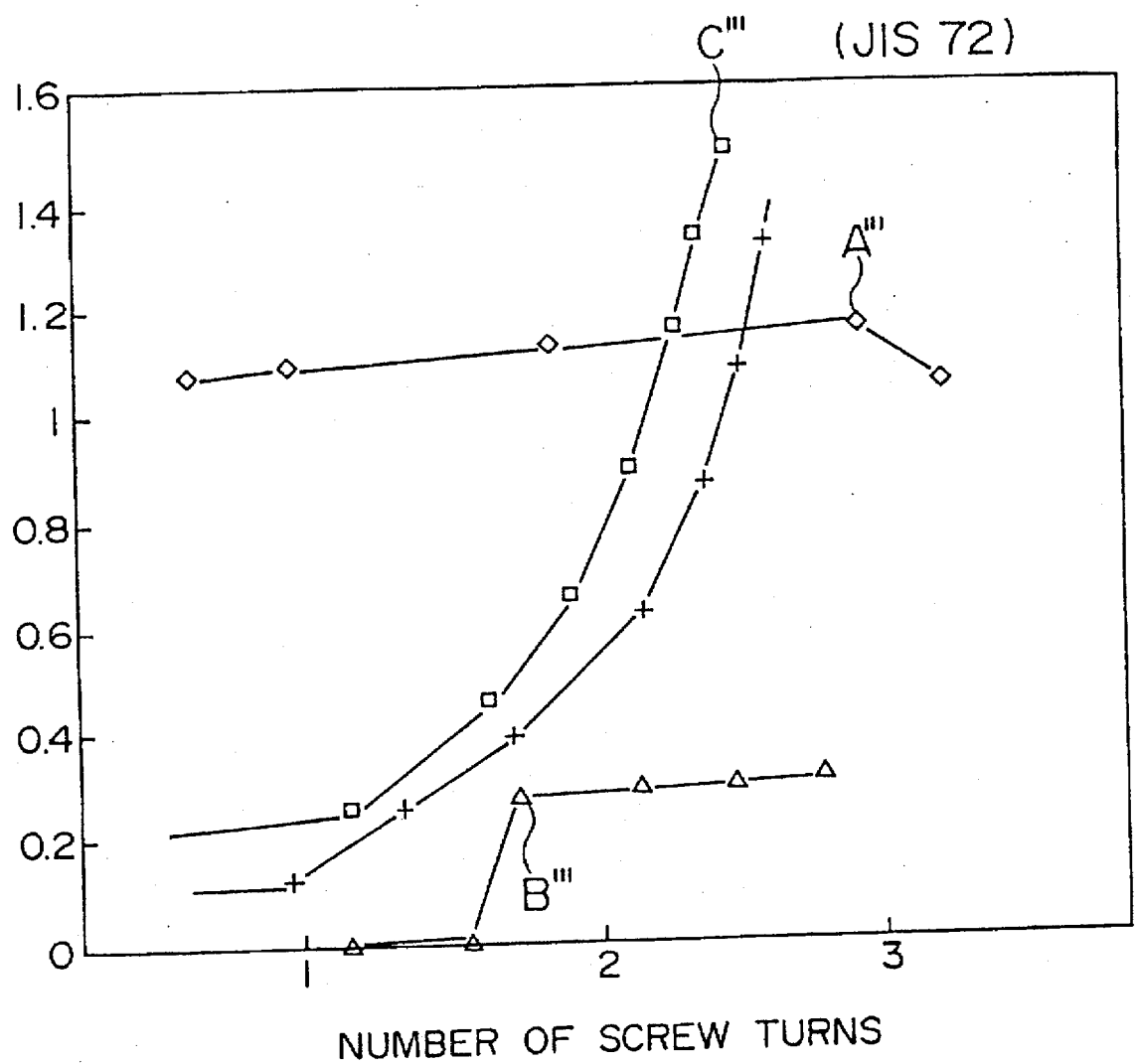
FIG. 22 is a graph showing the characteristic of a hemostatic valve according to another example of the present invention.

As shown in FIG. 22, at the position B''' one and a half turns before the position A''' where the catheter tube 24 was crushed, there is pressure resistance and the hemostatic characteristic is sufficient, but at the position C''' just before the position A'''the valve torque becomes strong and full tightening becomes difficult.

Comparative Example 2

The characteristics of the hemostatic valve were tested in the same way as in Example 3 except that use was made of a rubber tube of a JIS hardness of 32 as the holding ring 48. The results are shown in FIG. 19.

Figure 19:
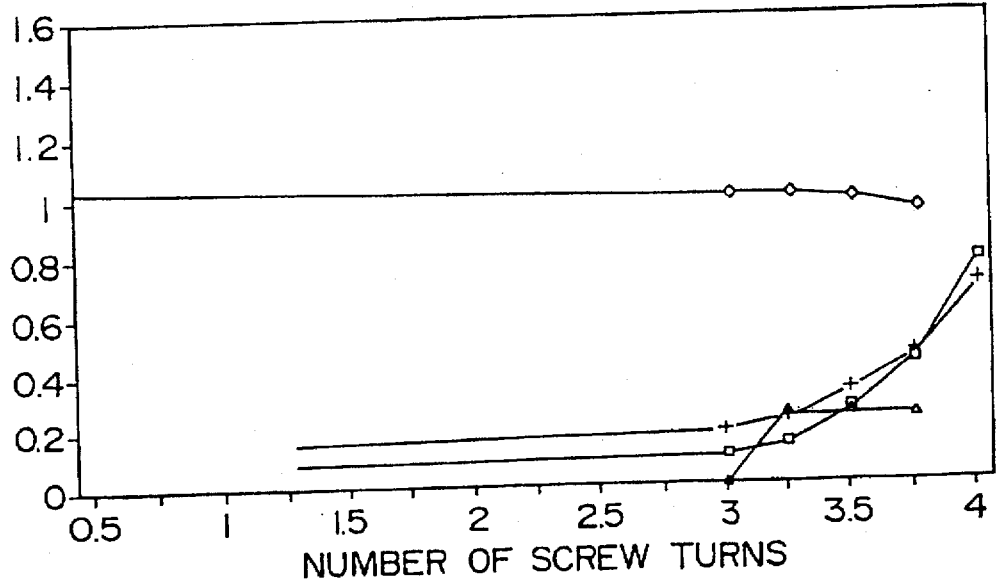
FIG. 19 is a graph showing the characteristic of a hemostatic valve according to a comparative example of the present invention.

As shown in FIG. 19, even at a position just before the catheter tube 24 is crushed, the valve torque and catheter holding force are weak and the catheter tube 24 is easily crushed. Also, the fixing force is weak. The functions required for the hemostatic valve are not sufficiently met.

Comparative Example 3

As the catheter tube 24 shown in FIG. 1, a polyurethane tube of an outer diameter of 3.0 mm and a thickness of 280 μm was prepared. At the outer circumference of the catheter tube 24, the hemostatic valve 40 was attached. As the fixed ring 48 used for this hemostatic valve 40, use was made of a rubber tube of an outer diameter of 6.8 mm, an inner diameter of 3.2 mm, and a length in the axial direction of 4.3 mm. The hardness of the rubber tube was 43 by JIS hardness.

The hemostatic valve 40 was attached to the outer circumference of the catheter tube 24 and the cap portion 50 was screwed on the hemostatic valve body 46 so that the fixed ring 48 was compressed. The relationship with the number of turns, the change in the inner diameter of the catheter, the change in the catheter holding force, the change in the valve torque, and the change in the pressure resistance was investigated in the same way as in Example 3. The results are shown in FIG. 20.

Figure 20:
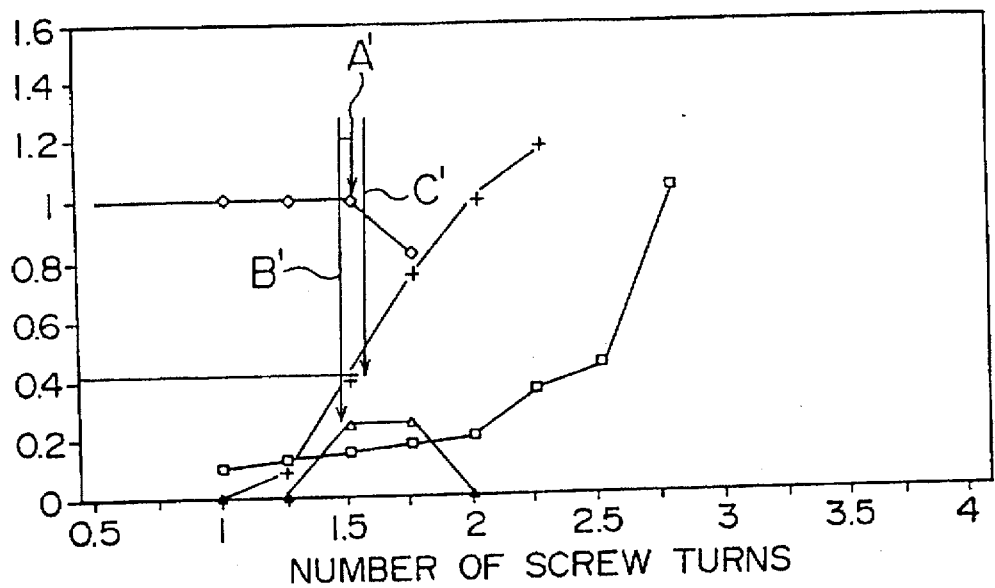
FIG. 20 is a graph showing the characteristic of a hemostatic valve according to a comparative example of the present invention.

As shown in FIG. 20, in the hemostatic valve 40 of the present example, at the position B' just before the position A' where the catheter tube 24 is crushed, the pressure resistance rises and a hemostatic action occurs. Therefore, this catheter tube 24 is easily crushed and if not crushed might not have a satisfactory hemostatic action. Further, when further screwed in, the pressure resistance falls. Also, even at a position C' near the position A' where the catheter tube 24 is crushed, only a catheter holding force of about 0.4 kg can be obtained and the fixing force is insufficient as well.

Comparative Example 4

The characteristics of the hemostatic valve were tested in the same way as in Comparative Example 3 except that use was made of a rubber tube of a JIS hardness of 50 as the holding ring 48. The results are shown in FIG. 21.

Figure 21:
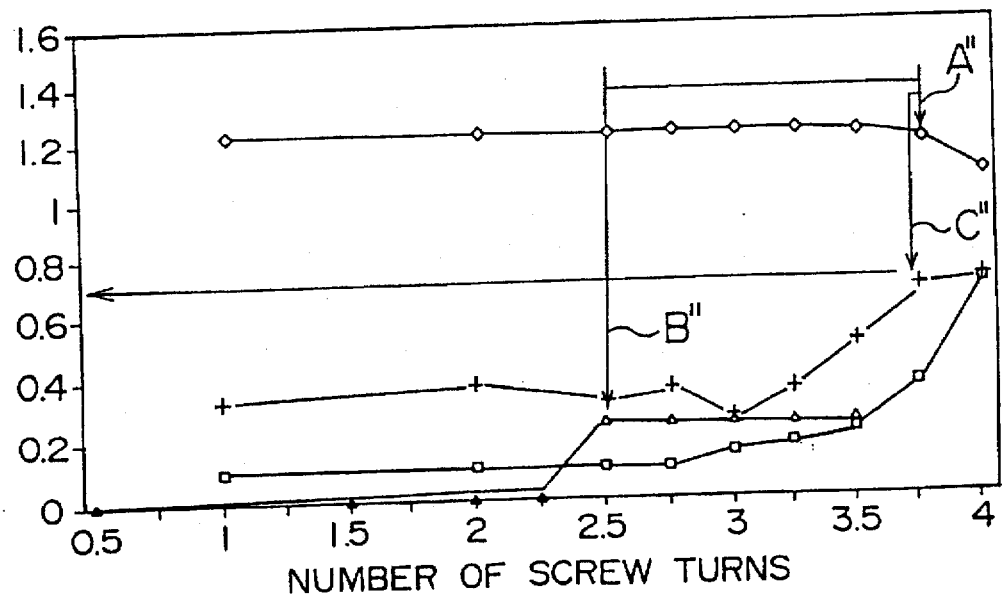
FIG. 21 is a graph showing the characteristic of a hemostatic valve according to another comparative example of the present invention.

As shown in FIG. 21, at the position B'' one and a half turns before the position A'' where the catheter tube 24 was crushed, there is pressure resistance and the hemostatic characteristic is sufficient, but at the position C'' just before the position A''the valve torque and the catheter holding force are weak and the catheter tube 24 is easily crushed. Further, the fixing force is weak. The functions required for a hemostatic valve are not sufficiently met.

Evaluation

Comparing the above Example 3 and Comparative Examples 2 to 4it is learned that with a JIS hardness of the holding ring 48 of less than 50functions sufficiently satisfactory for a hemostatic valve are not obtained, while at over 52 or so, the functions required for a hemostatic valve are satisfied with a good balance.

Example 5

As the inner tube 230 shown in FIG. 13, use was made of a fine stainless steel tube of an outer diameter of 1.16 mm and a thickness of 85 μm. The distal end portion "Lb" was set to a Vicker's hardness of 170 by heat treatment. The range of the distal end portion "Lb" was 40 mm. The Vicker's hardness of the inner tube 30 other than at the distal end portion "Lb" was 350.

A balloon catheter was prepared using this fine stainless steel tube as the inner tube. As the balloon portion 222 of the balloon catheter, use was made of a polyurethane film of a thickness of 0.1 mm. The outer diameter at the time of expansion was 15 mm, the inner volume of the balloon portion was 30 cc, and the length in the axial direction was 230 mm. As the catheter tube 224, further, use was made of a polyurethane tube of an outer diameter of 3 mm and a thickness of 180 μm.

Figure 23:
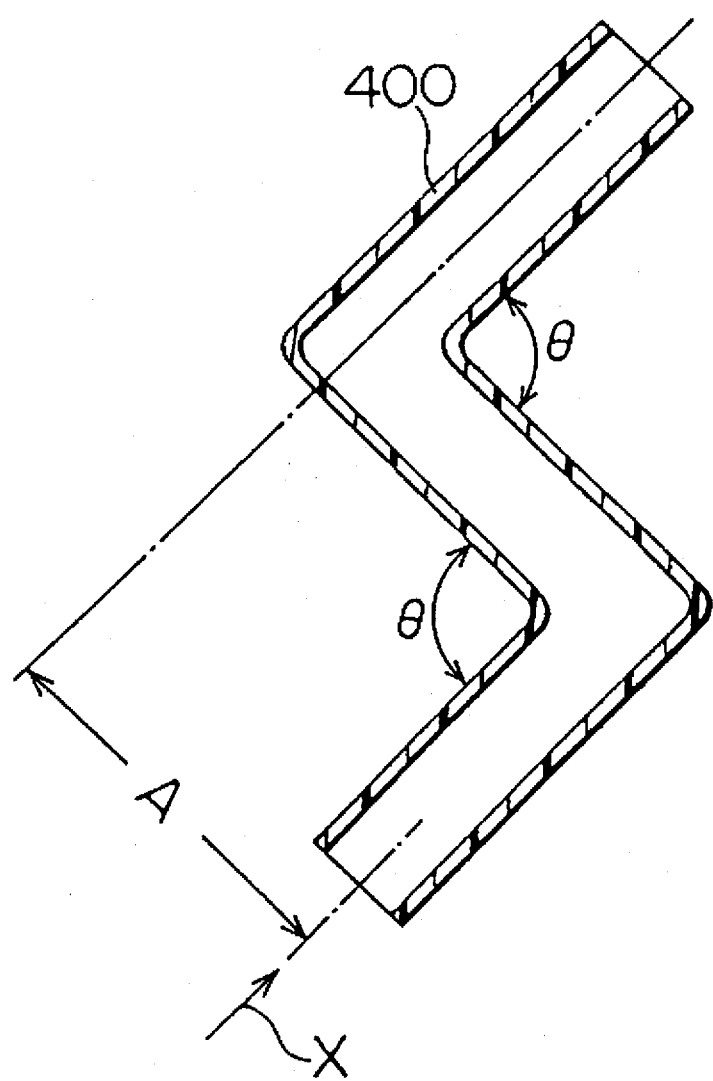
FIG. 23 is a cross-sectional view of a simulated blood vessel used for testing of an example of the present invention.

The balloon portion was compressed and wound on the inner tube of the balloon catheter. The distal end was inserted into the simulated blood vessel 400 shown in FIG. 23 from the direction of the arrow X with an insertion force of 3 kg. The insertability was tested and the results shown in Table 2. The denominator of the value showing the insertability in Table 2 indicates the number of times of the test, while the numerator indicates the number of successful insertions in the simulated blood vessel 400. A "successful insertion in the simulated blood vessel 400" means the state with the balloon catheter inserted from the X direction and the distal end of the balloon catheter passing through from the other end of the simulated blood vessel 400.

Note that as the simulated blood vessel 400, use was made of a polyvinyl chloride tube of an inner diameter of 35 mm and a thickness of 2 mm. The tube had two bent portions of angles Θ of 90° and a distance A between the bent portions of 100 mm.

TABLE 2

| | Insertability |
|---|---|
| Ex. 5 | 4/5 |
| Ex. 6 | 5/5 |
| Ex. 7 | 5/5 |
| Comp. Ex. 5 | 1/5 |

As shown in Table 2 in this example, there was successful insertion into the simulated blood vessel 400 four times out of five. The effectiveness of the present invention was confirmed.

Example 6

A balloon catheter was prepared in the same way as in Example 5 except that the distal end portion "Lb" of the fine stainless steel tube was heat treated in the same way as Example 5 and also was chemically polished by nitric acid to form a tapered thin portion, with the thinnest portion of the fine stainless steel tube being made 50 μm. This balloon catheter was used to conduct the same test as in Example 5. The results are shown in Table 2.

As shown in Table 2 in the present example, there was successful insertion into the simulated blood vessel 400 five times out of five. The effectiveness of the present invention was confirmed.

Example 7

A balloon catheter was prepared in the same way as in Example 5 except that the distal end portion "Lb" of the fine stainless steel tube was not only heat treated in the same way as Example 5 but also was given a simple bellows-like irregularity as shown in FIG. 15. This balloon catheter was used to conduct the same test as in Example 5. The results are shown in Table 2.

As shown in Table 2 in the present example, there was successful insertion into the simulated blood vessel 400 five times out of five. The effectiveness of the present invention was confirmed.

Comparative Example 5

A balloon catheter was prepared in the same way as in Example 5 using the same type of fine stainless steel tube as in Example 5 except that the distal end portion "Lb" was not treated in any way.

As shown in Table 2 in the present example, there was successful insertion into the simulated blood vessel 400 only one time out of five. It was confirmed that the insertability was poor.

We claim:

1. A balloon catheter comprising:

a balloon portion for insertion in an aorta for expansion and contraction;

a catheter tube connected to a proximal end of said balloon portion and formed therein with a shuttle gas passage for introducing and releasing a shuttle gas into and from said balloon portion;

an inner tube communicating with a blood port formed in a distal end of said balloon portion, said inner tube extending in said balloon portion and said catheter tube in an axial direction thereof, and having a blood passage therein formed separate from said shuttle gas passage of said catheter tube;

a bifurcation formed with a) a first passage formed with a shuttle gas port communicating with said shuttle gas passage of said catheter tube and b) a second passage formed with a blood pressure measurement port communicating with said blood passage in said inner tube, in said bifurcation, said first passage being disposed straight along the axial direction of said catheter tube and said second passage being disposed at a predetermined angle with respect to an axial center of said first passage; and an inner tube end holder attached to said second passage, said inner tube end holder holding a proximal end of said inner tube and disposing said inner tube eccentrically in said catheter tube wherein said inner tube contacts an inner wall of said catheter tube.

2. A balloon catheter according to claim 1 further comprising a hemostatic valve which can freely move in an axial direction on an outer circumference of an outside end of said catheter tube inserted into the blood vessel and the hemostatic valve can be affixed to the outer circumference of the catheter tube at any position in the axis direction of the catheter tube, said hemostatic valve comprising:

a hemostatic value body which is adapted to be attached to the outer circumference of the catheter tube in a manner freely movable along the axial direction;

a cap portion which is screwed with said hemostatic valve body and is adapted to be attached to the outer circumference of the catheter tube in a manner freely movable along the axial direction;

a holding ring which is adapted to be attached to the outer circumference of the catheter tube positioned between said hemostatic valve body and said cap portion, adapted to have a predetermined clearance with the outer circumference of the catheter tube in a state with said hemostatic valve body and cap portion not screwed together, and adapted to elastically deform to press against the outer circumference of the catheter tube by said hemostatic value body and said cap portion being screwed together more than a predetermined number of screw turns, Japanese Industrial Standard hardness of said holding ring being at least 52; and a hemostatic sheath portion connected to said hemostatic valve body, said hemostatic sheath portion being adapted to be attached to the outer circumference of the catheter tube in a manner freely movable in the axial direction and being adapted to be pushed in, at its distal end, into an insertion site of the blood vessel wherein the insertion site of the blood vessel is plugged by said hemostatic sheath portion.

3. A balloon catheter according to claim 1, wherein said inner tube is a metal inner tube, a distal end portion of said balloon portion being attached to an outer periphery of a distal end portion of said metal inner tube, and the distal end portion of said metal inner tube being formed thinner than other portions of said metal inner tube to improve its flexibility.

4. A balloon catheter according to claim 1, wherein said inner tube is a metal inner tube, a distal end portion of said balloon portion being attached to an outer periphery of a distal end portion of said metal inner tube, and the distal end portion of said metal inner tube being formed with a bellows-like irregularity to improve its flexibility.

5. A balloon catheter according to claim 1, wherein said inner tube is a metal inner tube, a distal end portion of said balloon portion being attached to an outer periphery of a distal end portion of said metal inner tube, and the distal end portion of said metal inner tube being formed with slits to improve its flexibility.

6. A balloon catheter according to claim 1, wherein said inner tube is a metal inner tube, a distal end portion of said balloon portion being attached to an outer periphery of a distal end portion of said metal inner tube, and the distal end portion of said metal inner tube being set to a lower hardness by heat treatment than other portions of said metal inner tube to improve its flexibility.

7. The balloon catheter as set forth in claim 6, 3, 4 or 5, wherein the range of a distal end portion of said metal inner tube to improve its flexibility is 3 to 15 cm.

8. The balloon catheter as set forth in claim 6, wherein the lower hardness of the distal end portion of said metal inner tube is 10 to 60 percent of a hardness of said other portions of said metal inner tube.

9. A balloon catheter according to claim 1, further comprising:

a metal connecting tube having a first end joined to the proximal end of said balloon portion and a second end joined to a distal end of said catheter tube at an outer circumference so as not to superpose said catheter tube and said balloon portion on each other.

* * * * *